United States Patent [19]
Wheeler

[11] Patent Number: 5,994,317
[45] Date of Patent: Nov. 30, 1999

[54] QUATERNARY CYTOFECTINS

[75] Inventor: Carl J. Wheeler, Poway, Calif.

[73] Assignee: Vical Incorporated, San Diego, Calif.

[21] Appl. No.: 08/629,965

[22] Filed: Apr. 9, 1996

[51] Int. Cl.$^6$ .................................................. A61K 48/00
[52] U.S. Cl. ................................ 514/44; 435/6; 435/455;
435/458; 435/325; 424/1.21; 424/9.321;
424/417; 424/420; 427/2.14; 357/402.2
[58] Field of Search ...................... 514/44, 247; 424/450,
424/1.21, 9.321, 417, 420, 812; 435/6,
325, 455, 458; 536/23; 427/2.14; 357/402.2

[56] References Cited

U.S. PATENT DOCUMENTS

| | | | |
|---|---|---|---|
| 2,368,208 | 1/1945 | Epstein | 260/404.5 |
| 3,265,719 | 8/1966 | Cowen et al. | 260/404 |
| 4,864,060 | 9/1989 | Karalis et al. | 564/292 |
| 5,049,386 | 9/1991 | Eppstein et al. | 424/427 |
| 5,068,431 | 11/1991 | Karalis et al. | 564/301 |
| 5,144,060 | 9/1992 | Morita et al. | 560/170 |
| 5,264,618 | 11/1993 | Felgner et al. | 560/224 |
| 5,279,833 | 1/1994 | Rose | 424/450 |
| 5,334,761 | 8/1994 | Gebeyehu et al. | 564/197 |
| 5,459,127 | 10/1995 | Felgner et al. | 514/7 |
| 5,614,548 | 3/1997 | Piantadosi et al. | 514/440 |
| 5,753,613 | 5/1998 | Ansell et al. | 514/2 |

FOREIGN PATENT DOCUMENTS

| | | |
|---|---|---|
| 2651898 A1 | 5/1978 | Germany . |
| WO 90/04918 | 5/1990 | WIPO . |
| WO 91/15501 | 10/1991 | WIPO . |
| PCT/US94/13362 | 11/1994 | WIPO . |
| PCT/US94/13428 | 11/1994 | WIPO . |

OTHER PUBLICATIONS

Bhattacharya et al. (Chemistry and Physics of Lipids, 78, 177–188, 1995).
Bhattacharya et al. (Langmuir, 11, 4748–4757, 1995).
Guo et al. (J. Liposome, 3, 1, 51–70, 1993, HCAPLUS, AN: 1993:546446).
Dorn et al., Chem., Rapid Commun, 4, 8, 513–17, HCA-PLUS, AN: 1983:535872.
Wheeler et al. (Biochim. et Biophsica Acta 1280, 1996, 1–11).
Meyer et al. (J. Med. Chem., 1991, 34:1377–1383).
"Synthesis of Amphiphilic Piperidinium Derivatives. Cationic Lipids 4[1]," Solodin, Igor and Heath, Timothy D., Synlett, p. 619, Jul. 1996 (received for publication Oct. 11, 1995).

"Synthesis of Amphiphilic Derivatives of N–Methyldiethanolamine. Cationic Lipids 5[1]," Solodin, et al., Synlett, p. 620, Jul. 1996 (received for publication Oct. 11, 1995).
"Synthesis of Novel Cationic Lipids with a Guanidine Group. Cationic Lipids 3[1]," Solodin, Igor and Heath. Timothy D., Synlett, pp. 617–618, Jul. 1996 (received for publication Sep. 19, 1995).
S. L. Morris–Natschke, et al., Synthesis of phosphocholine and quaternary amine ether lipids and evaluation of in vitro antineoplastic activity, Journal of Medicinal Chemistry, vol. 36, No. 14, pp. 2018–2025, (1993).
I. Solodin, et al. "Synthesis of amphiphilic derivatives of N–methyldiethanolamine. Cationic lipids. 5", Synlett, p. 620, (Jul. 1996).
Y. Fukuyama, et al., "Electroviscous fluids for clutch or shock absorbers", Chemical Abstracts, vol. 116, No. 16, p. 203, abstract No. 155243u, Apr. 20, 1992.
I.P. Komkov, et al., "Surface–active quaternary ammonium salts.", Chemical Abstracts, vol. 77, No. 22, p. 92, abstract No. 141711j, Nov. 27, 1972.
H. Distler, et al., "Biocidal surfactants", Chemical Abstracts, vol. 71, No. 23, p. 113, abstract No. 110160a, Dec. 8, 1969.
G. Nabel, et al., "Immunotherapy of Malignancy by In Vivo Gene Transfer into Tumors", Human Gene Therapy, 3:399–410, (1992).
A. Rosenthal, et al., "A Synthetic Inhibitor of Venom Lecithinase A*", The Journal of Biological Chemistry, vol. 235, No. 8, (1960).
P. Felgner, et al., "Lipofection: A highly efficient, lipid–medicated DNA–transfection procedure", Proc. Natl. Acad. Sci. USA, 84:7413–7417 (1987).
J. Felgner, et al., "Enhanced Gene Delivery and Mechansim Studies with a Novel Series of Cationic Lipid Formulations*", The Journal of Biological Chemistry, 269:2550–2561 (1994).
C. Wheeler, et al., "Converting an alcohol to an amine in a cationic . . . ultrastructure of DNA–cytofectin complexes", BBA, 1280:1–11 (1996).

*Primary Examiner*—Bruce R. Campell
*Assistant Examiner*—Dave Trong Nguyen
*Attorney, Agent, or Firm*—Knobbe, Martens, Olson & Bear, LLP

[57] ABSTRACT

Cationic lipids, having a derivatized quaternary ammonium head group, that provide improved cell targeting ability and enhanced transfective efficacy for the delivery of molecules into cells. The lipids comprise a linker having functional groups that provide sites for further attachment of drugs, cell receptor ligands or other bioactive agents.

38 Claims, 9 Drawing Sheets

Total Expression (COS7)

Peak Expression (COS7)

Total Expression (C2C12)

Peak Expression (C2C12)

QUATERNARY CYTOFECTINS

The present invention relates to complex amphiphilic lipids. It relates particularly to complex cationic lipids comprising a quaternary ammonium group.

BACKGROUND OF THE INVENTION

Cationic lipids are amphiphilic molecules having a lipophilic region, commonly comprising one or more hydrocarbon or alkyl groups, and a hydrophilic region comprising at least one positively charged polar head group. Cationic lipids are useful for facilitating the transport of macromolecules through the plasma membrane of cells and into the cytoplasm by forming net positively charged complexes. The process, which can be carried out in vivo as well as in vitro, is known as transfection, and the cationic lipids used in such techniques are known as cytofectins.

Cytofectins which enhance transfection efficiency to a statistically significant extent are beneficial. As little as a two fold increase over the activity obtained with naked DNA is beneficial, although preferably transfection efficiency is increased 5–10 fold, and more preferably transfection efficiency is enhanced more than 10 fold.

Typically, cytofectins are combined with a neutral zwitterionic lipid such as a phospholipid, because it has been found that the two amphiphilic lipid species in combination are able to form vesicles comprising ordered lipid bilayers that are more effective at transfection than the cytofectin alone. These vesicles, or liposomes, have multiple positive charges on the surface which allow them to form a complex with a polynucleotide or other anionic molecule such as negatively charged proteins. Remaining net cationic charges on the surface of the polynucleotide/cytofectin/neutral lipid complex are capable of strong interaction with the predominately negative charge of the cell membrane surface.

Apart from the basic features of amphiphilic properties and the polar head group, cytofectins have considerable structural diversity in the lipophilic and hydrophilic regions. Many different cytofectin species have been synthesized for use in transfection and are now commercially available. Such cytofectins include, for example, LIPOFECTIN® (a 1:1 w/w liposome formulation of the cationic lipid N-[1-(2, 3-dioleyloxy)propyl]-N,N,N-trimethylammonium chloride (DOTMA) and dioleolyl phosphatidylethanolamine (DOPE) in membrane filtered water), LIPOFECTACE™ (a 1:2.5 w/w liposome formulation of the cationic lipid dimethyl dioctadecylammonium bromide (DDAB) and dioleoyl phosphatidylethanolamine (DOPE)), LIPOFECTAMINE™ (a 3:1 w/w formulation of the polycationic lipid 2,3-dioleyloxy-N-[2(sperminecarboxamido)ethyl]-N,N-dimethyl-1-propanaminiumtrifluoroacetate (DOSPA), Chemical Abstracts name: N-[2({2,5-bis(3-aminopropyl)amino]-1-oxypentyl}amino)ethyl]-N-N-dimethyl-2-3-bis(9-octadecenyloxy)-1-propanaminium trifluoroacetate), and the neutral lipid dioleolyphosphatidylethanolamine (DOPE) in membrane filtered water), TRANSFECTAM® (dioctadecylamidoglycylspermine), and DOTAP™ (N-[1-(2,3-dioleoyloxy)propyl]-N,N,N-trimethylammonium methylsulfate). The structural diversity of effective cytofectins reflects, in part, the observation that structure-function-recognition aspects of cytofectins differ with respect to distinct applications in cells. Experience with cytofectins structurally similar to the DOTMA compounds indicates that transfection activity depends in part on the cell type transfected (Felgner et al. *J. Biol. Chem.* 84:7413–7417, 1987; Wheeler et al. Biochem. Biophys. Acta, in press). Particularly, cationic lipids comprising spermine substitution of the ammonium groups proved more effective than DOTMA for transfection of some cell lines. This phenomenon suggests that effective transfection depends not only on passive fusion of the cationic lipid complex with the structural lipid bilayer of the plasma membrane, but on specific cellular characteristics and interaction between cell components and the individual cationic lipid species.

Structural variants among cytofectin species are therefore an indication of a more sophisticated understanding of the multiple and complex interactions of cytofectins with cells, and an effort on the part of investigators to take advantage of one or more of these interactions.

DOTMA, N-[1-(2,3-dioleyloxy)propyl]-N,N,N-trimethyl ammonium, disclosed in U.S. Pat. No. 5,049,386 to Epstein, was one of the first cationic lipids developed, and lipids of this group have become reference compounds in evaluating comparative cytofectin potency in the development of new structural variants. DOTMA lipids are characterized by a propanaminium group having a quaternary nitrogen, which provides the cationic site of the molecule, together with a pair of $C_{18}$ hydrocarbons that are ether-linked to the propyl backbone of the molecule. The quaternary nitrogen is trisubstituted with relatively shorter alkyl chains, such as methyl groups. A structurally similar cationic lipid, 1,2-bis (oleoyloxy)-3-3-(trimethylammonia)propane (DOTAP), comprises acyl, rather than ether-linked alkyl groups, and is believed to be more easily metabolized by target cells.

Some species of cationic lipids, for example, ammonium salts directly substituted by alkyl or acyl groups, were developed primarily for purposes of economy (U.S. Pat. No. 5,279,833 to Rose). Others were developed in an effort to provide less toxic effects; for example, a highly biocompatible cytofectin prepared from phosphatidylcholine and sphingomyelin: 1,2-dioleoyl-sn-glycero-3-ethylphosphocholine (Avanti Polar Lipids, Inc. Alabaster, Ala., Cat. Nos. 890700–706).

U.S. Pat. No. 5,264,618 to Felgner et al. discloses cytofectins that are structurally similar to the Rosenthal Inhibitor (RI) of phospholipase A (Rosenthal et al., *J. Biol. Chem.* 235:2202–2206, 1960) and diacyl- or alkyl/acyl-species thereof. Rosenthal Inhibitor based cytofectins are characterized by having a substituent with the structure

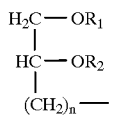

linked to a quaternary nitrogen.

The RI based series of compounds are known by acronyms having the pattern: DORIE ($C_{18}$); DPRIE ($C_{16}$); and DMRIE ($C_{14}$). These acronyms imply a common basic chemical structure; for example, DMRIE is 1-propanaminium, N-(2-hydroxyethyl)-N,N-dimethyl-2,3-bis(tetradecyloxy)-, bromide, (±)-(CAS registry:146659); the others differ in their substituent alkyl groups. These cytofectins, having a polar hydroxyethyl substituent on the quaternary ammonium group, provide more effective transfection in many cases than DOTMA type compounds. A study of the effect of varying substituents at the hydroxyalkyl moiety and variation of alkyl chain lengths on the transfection efficacy of the RI cytofectins is presented in Felgner et al. (*J. Biol. Chem.* 269:2550–2561, 1994). Again, the studies showed that the optimum hydroxyl alkyl chain length is cell-type dependent.

The conversion of DMRIE to βAE-DMRIE (Wheeler et al., Biochem. Biophys. Acta, in press) has been found to have a significant effect on cytofectin activity. DMRIE, which has a quaternary nitrogen adjacent to a primary alcohol, thus imparting a pH independent positive charge, is one of the most active cytofectins now known. However, the substitution of a primary amine group for the alcohol on DMRIE to give βAE-DMRIE was found to form DNA complexes that are structurally distinct from those with DMRIE, and βAE-DMRIE is able to transfect many cell lines effectively in the absence of helper co-lipids. The observation that a single substitution in the cytofectin skeleton can provide marked changes in transfection properties suggests that other modifications can bring about similar improvements in gene delivery.

Continuing studies of the transfection event indicate that cationic lipids may facilitate not only entry of the functional molecule into the cytoplasm of a cell, but may also provide additional beneficial capabilities; for example, protecting the functional molecule from lysosomal degradation, facilitating entry into the nuclear compartment, or even preventing the degradation of the RNA transcription product by cytoplasmic enzymes. These functions of cationic molecules are believed to be related to specific structural features. Accordingly, there is a need for cytofectins that are particularly suited to transfection of foreign molecules into specific cell types. There is also a need to develop cytofectins that are able to perform specific intracellular functions.

SUMMARY OF THE INVENTION

The present invention provides a new category of cytofectins having the common characteristic of possessing a quaternary nitrogen.

One embodiment of the present invention are compounds having the formula $$(Z-Y-(CH_2)_n)_p - \overset{+}{N} - ((CH_2)_m - X - R)_q \quad W^-$$

wherein

R is H, linear, branched, unsubstituted or substituted $C_1-C_{23}$ alkyl, acyl, alkene, or heteroalkyl groups having from 0 to 6 sites of unsaturation and containing from 0 to 5 heteroatoms, or cyclic or aryl groups each of which may contain 0–5 heteroatoms;

X is absent, O, N, NH, S, or Se;

Y is absent, H, O, N, S, Se, NH or R as defined above;

Z is H, O, N, S, NH, R as defined above, or an amino acid, peptide, polypeptide, protein, nucleic acid, nucleotide or nucleoside, polynucleotide, polynucleoside, mono-, di- or polysaccharaide, or other bioactive or pharmaceutical agent or the following structure:

$$\begin{array}{c} R_{10} \diagdown_T \diagup R_9 \\ \| \\ -G-\overset{R_8}{\underset{R_5}{\overset{|}{C}}}A{\overset{R_8}{\underset{R_6}{\diagdown R_7}}} \end{array}$$

wherein $R_5$ through $R_{10}$ are independently absent, H, linear, branched, unsubstituted or substituted $C_1-C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR;

T is O, N, S, Se, or C;

A is O, N, S, Se, or C;

W is a pharmaceutically acceptable anion.

n is 0–10;

m is 0–4;

the sum of p and q is 4;

wherein the compound is not a Rosenthal Inhibitor based cytofectin.

In a preferred embodiment of compounds of the structure above, n is 1–10 and m is 2–4. In another preferred embodiment X is O. In a further preferred embodiment, q is 1, 2, or 3. Advantageously, Z is H and Y is absent.

Another embodiment of the present invention is a compound of the formula $$\begin{array}{c} R_1-X_1-(CH_2)_m \\ R_2-X_2-(CH_2)_p - \overset{+}{N} - (CH_2)_n - R_4 \quad W^- \\ R_3-X_3-(CH_2)_q \end{array}$$

wherein $R_1$, $R_2$, and $R_3$ are independently H, linear, branched, unsubstituted or substituted $C_1-C_{23}$ alkyl, acyl, alkene, or heteroalkyl groups having from 0 to 6 sites of unsaturation and containing from 0 to 5 heteroatoms, or cyclic or aryl groups;

$X_1$, $X_2$, and $X_3$ are independently absent or are H, O, N, NH, S or Se;

$R_4$ is H, OH, $NH_2$ or the following structure $$\begin{array}{c} R_{10} \diagdown_T \diagup R_9 \\ \| \\ -G-\overset{R_8}{\underset{R_5}{\overset{|}{C}}}A{\overset{R_8}{\underset{R_6}{\diagdown R_7}}} \end{array}$$

wherein $R_5$ through $R_{10}$ are independently absent, H, linear, branched, unsubstituted or substituted $C_1-C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR, where R is as defined for $R_1$, $R_2$, and $R_3$ above;

T is O, N, S, Se, or C;

A is O, N, S, Se, or C;

m, p, and q are independently 0–4;

n is 0–10;

W is a pharmaceutically acceptable anion;

wherein the compound is not a Rosenthal Inhibitor based cytofectin.

A further embodiment is a compound of the formula

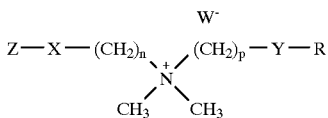

wherein

X is absent, O, N, NH, S, or Se;

Y is absent, O, N, NH, S, or Se;

Z is H, linear, branched, unsubstituted or substituted $C_1$–$C_{23}$, alkyl, acyl, alkene, or heteroalkyl groups having from 0 to 6 sites of unsaturation and containing from 0 to 5 heteroatoms, or cyclic or aryl groups, or an amino acid, nucleotide, polynucleotide, mono-, di- or polysaccharide, or other bioactive or pharmaceutical agent or the following structure:

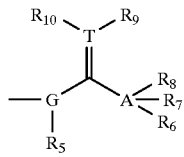

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR where R is as defined below;

T is O, N, S, Se, or C;

A is O, N, S, Se, or C;

R is H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups;

n is 0–10;

p is 0–4;

W is a pharmaceutically acceptable anion;

wherein the compound is not a Rosenthal Inhibitor based cytofectin.

In a preferred embodiment of the structure above, Y is O. In a further preferred embodiment of the structure above, p is 2.

In yet other preferred embodiments, the MEMO class of compounds, R is $C_{14}H_{29}$. Preferentially, in the structure above Z is H and X is selected from the group consisting of absent, O and NH. In further preferred compounds of the MEMO class n is 2–6.

Further embodiments of the invention are compounds of the DEXO series having the formula

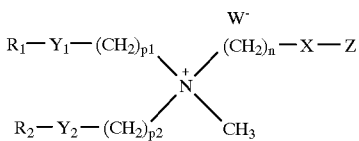

wherein

X is absent, O, N, NH S, or Se;

$Y_1$ and $Y_2$ are independently absent, O, N, NH, S, or Se;

Z is H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups, or an amino acid, nucleotide, polynucleotide, mono-, di- or polysaccharide, or other bioactive or pharmaceutical agent or the following structure:

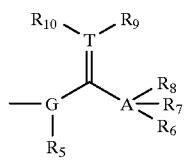

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR where R is as defined for $R_1$ and $R_2$ below;

T is O, N, S, Se, or C;

A is O, N, S, Se, or C;

$R_1$ and $R_2$ are independently H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups;

n is 0–10;

$p_1$ and $p_2$ are independently 0–4;

W is a pharmaceutically acceptable anion;

wherein the compound is not a Rosenthal Inhibitor based cytofectin.

In preferred embodiments of the above structure Y is O. In additional preferred DEXO compounds, $p_1$ and $p_2$ are 2.

Preferred compounds of the DEXO series are the DEDO class of compounds wherein R is $C_{10}H_{21}$. Preferred members of the DEDO class are those wherein Z is H and X is selected from the group consisting of absent, O and NH. In additional preferred DEDO compounds, n is 2–10. PA-DEDO, in which Z is H, X is NH, n is 3, $p_1$, and $p_2$ are 2, and $Y_1$ and $Y_2$ are O, is the most active member of the DEDO class in the murine lung assay, although its activity in this assay is not as great as that of some members of the DELO class.

Further preferred embodiments of the DEXO series are the DELO class of compounds wherein R is $C_{12}H_{25}$. Advantageous members of the DELO class are those wherein Z is H and X is selected from the group consisting of absent, O and NH. Additional advantageous DELO class compounds are those wherein n is 2–10. HA-DELO, in which Z is H, X is NH, n is 6, $p_1$ and $p_2$ are 2, and $Y_1$ and $Y_2$ are O, is particularly effective in the murine lung assay, exhibiting activity greater than numerous DEMO, DELO, DEDO, TELO, and TECO compounds against which it was compared. Gly-P-DELO, in which X is NH, Z is glycine amide, n is 3, and $Y_1$ and $Y_2$ are O, has also proven effective in the murine lung assay. PA-DELO, in which Z is H, X is NH, n is 3, $p_1$ and $p_2$ are 2, and $Y_1$ and $Y_2$ are O, has demonstrated efficacy in the porcine intraarterial assay.

Further preferred embodiments of the DEXO series are the members of the DEMO class in which R is $C_{14}H_{29}$. In preferred members of the DEMO class, Z is H and X is selected from the group consisting of absent, O and NH. In additional preferred members of the DEMO class n is 2–10. PA-DEMO, in which Z is H, X is NH, n is 3, $p_1$ and $p_2$ are 2, and $Y_1$ and $Y_2$ are O, has proven particularly effective in the murine intraperitoneal assay.

Additional embodiments of the present invention are the TEXO series of compounds having the formula:

$$R_1-Y_1-(CH_2)_{p1} \diagdown \underset{N}{\overset{+}{}} \diagup (CH_2)_n-X-Z$$
$$R_2-Y_2-(CH_2)_{p2} \diagup \diagdown (CH_2)_{p3}-Y_3-R_3$$

$W^-$ wherein

X is absent, O, N, NH, S, or Se;

$Y_1$, $Y_2$ and $Y_3$ are independently absent, O, N, NH, S, or Se;

Z is H, linear, branched, unsubstituted or substituted $C_1-C_{23}$ alkyl, acyl, alkene, or heteroalkyl groups having from 0 to 6 sites of unsaturation and containing from 0 to 5 heteroatoms, or cyclic or aryl groups, or an amino acid, nucleotide, polynucleotide, mono-, di- or polysaccharide, or other bioactive or pharmaceutical agent or the following structure:

$$R_{10} \diagdown_T \diagup R_9$$
$$-G-A\underset{R_6}{\overset{R_8}{\diagdown R_7}}$$
$$R_5$$

wherein $R_5$ through $R_{10}$ are independently absent, H, linear, branched, unsubstituted or substituted $C_1-C_{23}$, alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR where R is as defined for $R_1$, $R_2$, and $R_3$ below;

T is O, N, S, Se, or C;

A is O, N, S, Se, or C;

$R_1$, $R_2$, and $R_3$ are independently H, linear, branched, unsubstituted or substituted $C_1-C_{23}$ alkyl, acyl, alkene, or heteroalkyl groups having from 0 to 6 sites of unsaturation and containing from 0 to 5 heteroatoms, or cyclic or aryl groups;

n is 0–10;

$p_1$, $p_2$ and $p_3$ are independently 0–4;

W is a pharmaceutically acceptable anion;

wherein the compound is not a Rosenthal Inhibitor based cytofectin.

In preferred members of the TEXO series, $Y_1$, $Y_2$ and $Y_3$ are O. In further preferred TEXO compounds $p_1$, $p_2$ and $p_3$ are 2.

Preferred members of the TEXO series are the TELO class of compounds wherein R is $C_{12}H_{25}$. Preferred TELO class compounds are those wherein Z is H and X is selected from the group consisting of absent, O and NH. In additional preferred TELO compounds, n is 2–10. PA-TELO, in which Z is H, X is NH, n is 3, $p_1$, $p_2$ and $p_3$ are 2, and $Y_1$, $Y_2$, and $Y_3$ are O has proven particularly effective in the Renca tumor assay.

Further preferred members of the TEXO series are the TEDO class of compounds wherein R is $C_{10}H_{21}$. In preferred TEDO compounds, Z is H and X is selected from the group consisting of absent, O and NH. Additional preferred TEDO compounds are those wherein n is 2–10.

Further preferred members of the TEXO series are the compounds of the TECO class wherein R is $C_8H_{17}$. In preferred TECO compounds, Z is H and X is selected from the group consisting of absent, O and NH. Additional preferred TECO compounds are those wherein n is 2–10.

The present invention also encompasses a method for delivering a molecule into a sell comprising the steps of (a) contacting the molecule with a formulation comprising an effective amount of any of the cationic lipids of claim 1 to form a complex with the lipid; and (b) contacting a cell with the lipid complex formed in step (a);

whereby a biologically effective amount of the molecule is inserted into the cell.

In a preferred embodiment of the above method, the molecule delivered into the cell comprises an anionic molecule.

In some embodiments of the above method the formulation additionally includes one or more additional lipids. Preferentially, the additional lipids are selected from the group consisting of neutral lipids, phospholipids, and cholesterol.

In one embodiment of the above method the cells are in vitro. In another embodiment of the above method cells are in vivo.

In a preferred embodiment of the method wherein the cells are in vivo, the cells are used in an assay selected from the group consisting of murine lung transfection, murine intraperitoneal tumor, murine intramuscular and porcine or rabbit intraarterial assays.

DETAILED DESCRIPTION OF THE INVENTION

Figure 1:
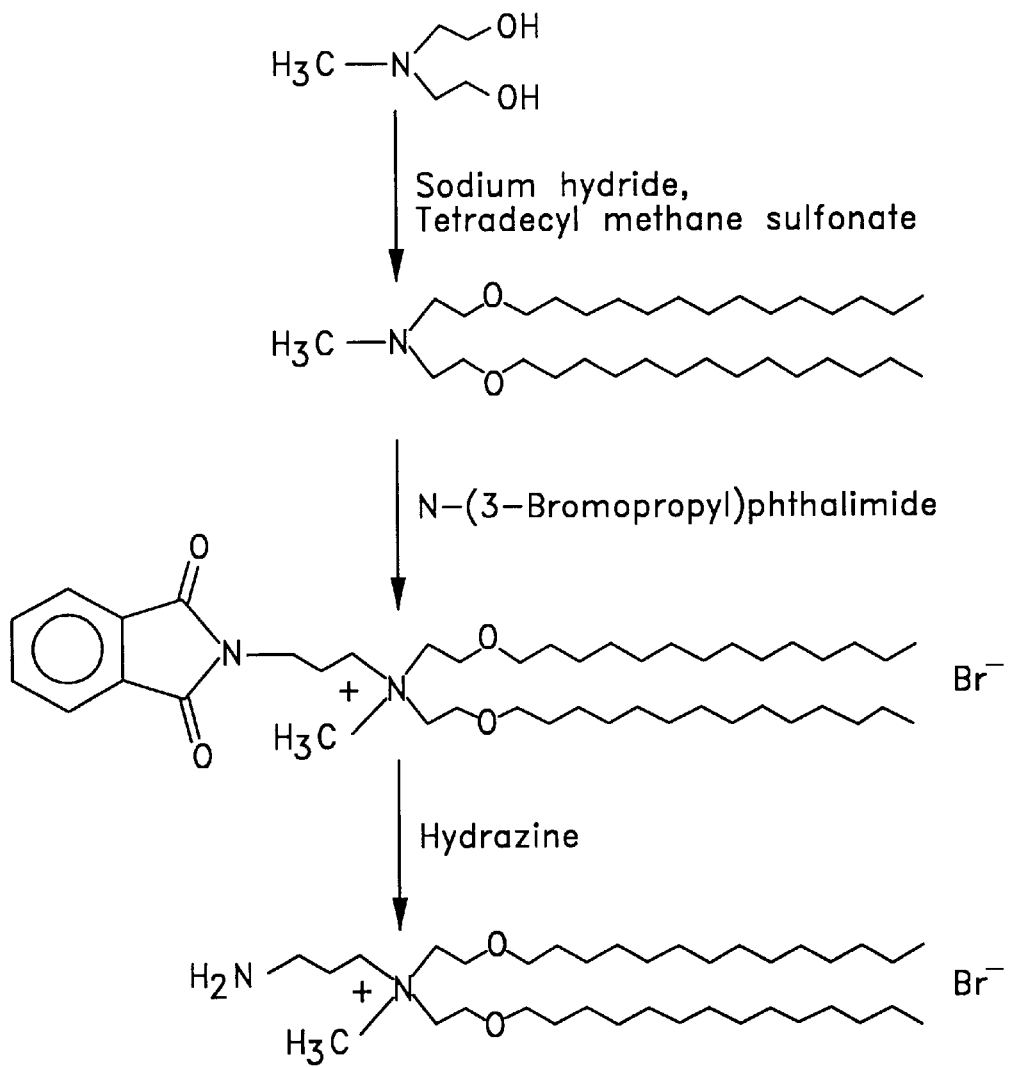
FIG. 1 illustrates the basic synthetic pathway for the quaternary cytofectins of the present invention using [(3-aminopropyl)-(bis-(2-tetradecyloxyethyl))-methylammonium bromide] (PA-DEMO) as a representative example.
Figure 2A:
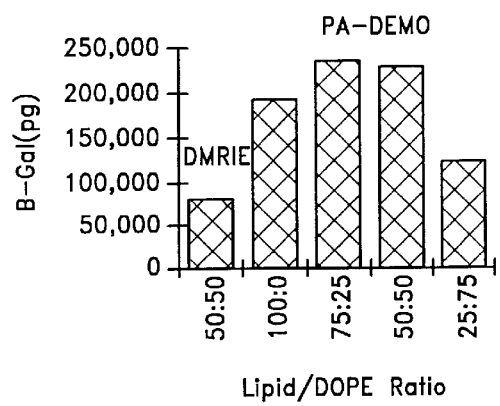
FIGS. 2A–2D compare the transfection efficiency of PA-DEMO and DMRIE in two cell lines, COS7 and $C2C_{12}$ cells in formulations having varying ratios of lipid:DOPE.
Figure 2B:
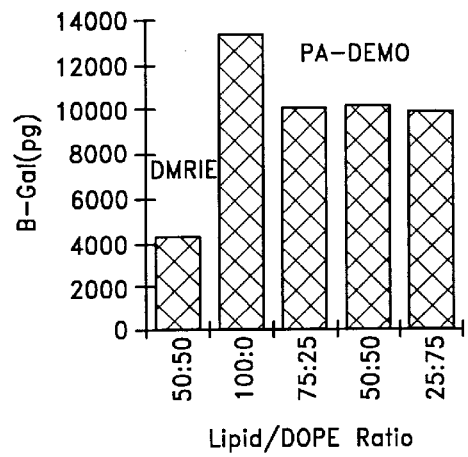
Figure 2C:
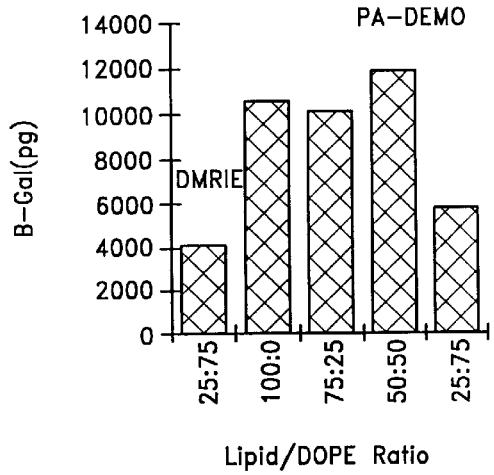
Figure 2D:
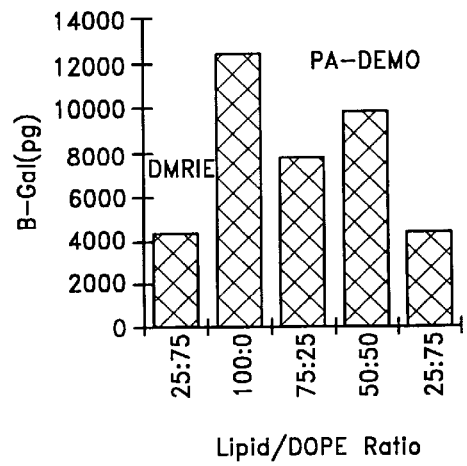

It has been discovered that quaternary nitrogen compounds are effective cytofectins which may have advantageous characteristics resulting from their specific structures. These compounds can be derivatized to form transfection agents having the ability to interact more specifically with the cell membrane and to achieve higher levels of transfection. They provide structures that can be adapted to target key receptors and enzymes of cellular surfaces and are thus suitable for use in the discovery and exploitation of important factors in molecular recognition. Some of these cationic lipids can also be attached to substances that are delivered intracellularly for achieving a particular biological purpose.

The cationic lipids of the present invention share a quaternary nitrogen to which a functional group may be appended through an alkyl linker. The functional group may consist of carbamyl, carboxyl, ureyl, thiol, ester, ether, thioureyl, phosphoryl, or guanidyl groups which can be used either (1) to attach a cell targeting moiety or (2) to attach a therapeutic molecule to the cytofectin. Additionally or alternatively, the functional group can be used as a linker to attach groups that can increase the polar charge density of the cytofectin, thus enhancing transfection.

Structure: Quaternary Nitrogen

The quaternary nitrogen compounds of the present invention include the MEXO, DEXO, and TEXO series of compounds. In the MEXO series of compounds, there is a single ether, ester, sulfide, amine, or selenyl linked hydrocarbon chain joined to the quaternary nitrogen through an alkyl linker. The DEXO series of compounds has two ether, ester, sulfide, amine, or selenyl linked hydrocarbon chains joined to the quaternary nitrogen through alkyl linkers. In the TEXO series of compounds there are three ether, ester, sulfide, amine or selenyl linked hydrocarbon chains joined to the quaternary nitrogen through an alkyl linker. Each series of compounds encompasses several classes of compounds. In those compounds designated MEMO and DEMO, the ether, ester, sulfide, amide, or selenyl linked hydrocarbon chain is $C_{14}H_{29}$. In those compounds designated DEDO and TEDO the ether, ester, sulfide, amide, or selenyl linked hydrocarbon chain is $C_{10}H_{21}$. In those compounds designated DELO and TELO, the ether, ester, sulfide, amide, or selenyl linked hydrocarbon chain is $C_{12}H_{25}$. In those compounds designated TECO, the ether, ester, sulfide, amide, or selenyl linked hydrocarbon chain is $C_8H_{17}$.

Table I below provides examples of particular compounds and their acronyms. The acronyms provided in Table I refer to compounds in which p+q=3 having the general formula:

$$(R-O-(CH_2)_2)_p - \overset{+}{N} - ((CH_2)_n - X$$
$$\underset{(CH_3)_q}{|} \quad W^-$$

| | |
|---|---|
| HE-MEMO | R = $C_{14}H_{29}$, X = OH, n = 2, p = 1 |
| PA-MEMO | R = $C_{14}H_{29}$, X = $NH_2$, n = 3, p = 1 |
| BA-MEMO | R = $C_{14}H_{29}$, X = $NH_2$, n = 4, p = 1 |
| DMA-DEDO | R = $C_{10}H_{21}$, X = H, n = 1, p = 2 |
| HE-DEDO | R = $C_{10}H_{21}$, X = OH, n = 2, p = 2 |
| EA-DEDO | R = $C_{10}H_{21}$, X = $NH_2$, n = 2, p = 2 |
| PA-DEDO | R = $C_{10}H_{21}$, X = $NH_2$, n = 3, p = 2 |
| BA-DEDO | R = $C_{10}H_{21}$, X = $NH_2$, n = 4, p = 2 |
| FA-DEDO | R = $C_{10}H_{21}$, X = $NH_2$, n = 5, p = 2 |
| DMA-DELO | R = $C_{12}H_{25}$, X = H, n = 1, p = 2 |
| HE-DELO | R = $C_{12}H_{25}$, X = OH, n = 2, p = 2 |
| EA-DELO | R = $C_{12}H_{25}$, X = $NH_2$, n = 2, p = 2 |
| PA-DELO | R = $C_{12}H_{25}$, X = $NH_2$, n = 3, p = 2 |
| BA-DELO | R = $C_{12}H_{25}$, X = $NH_2$, n = 4, p = 2 |
| FA-DELO | R = $C_{12}H_{25}$, X = $NH_2$, n = 5, p = 2 |
| HA-DELO | R = $C_{12}H_{25}$, X = $NH_2$, n = 6, p = 2 |
| PMU-DELO | R = $C_{12}H_{25}$, X = NH—C=O—$NHCH_3$, n = 3, p = 2 |
| Lys-P-DELO | R = $C_{12}H_{25}$, X = NH-lysine amide, n = 3, p = 2 |
| Boc-Lys-P-DELO | R = $C_{12}H_{25}$, X = NH-α(Benzyloxycarbonyl)lysine amide, n = 3, p = 2 |
| Lys(CBz)-P-DELO | R = $C_{12}H_{25}$, X = NHε-(Carbobenzyloxy)-lysine amide, n = 3, p = 2 |
| Gly-P-DELO | R = $C_{12}H_{25}$, X = NH-glycine amide, n = 3, p = 2 |
| Orn-P-DELO | R = $C_{12}H_{25}$, X = NH-ornithine amide, n = 3, p = 2 |
| Boc-Orn-P-DELO | R = $C_{12}H_{25}$, X = NH-α(Benzyloxycarbonyl)-ornithine amide, n = 3, p = 2 |
| Orn-(CBz)-P-DELO | R = $C_{12}H_{25}$, X = NH-ε-(Carbobenzyloxy)-ornithine amide, n = 3, p = 2 |
| DELOx-Pro-Am | R = $C_{12}H_{25}$, X = —C(O)$NHCH_2CH_2CH_3$, n = 1, p = 2 |
| DELOx-Arg(NO2)-OMe | R = $C_{12}H_{25}$, X = C(O) (ε-nitro arginine methyl ester) αamide n = 1, p = 2 |
| DMA-DEMO | R = $C_{14}H_{29}$, X = H, n = 1, p = 2 |
| HE-DEMO | R = $C_{14}H_{29}$, X = OH, n = 2, p = 2 |
| PA-DEMO | R = $C_{14}H_{29}$, X = $NH_2$, n = 3, p = 2 |
| HE-TELO | R = $C_{12}H_{25}$, X = OH, n = 2, p = 3 |
| PA-TELO | R = $C_{12}H_{25}$, X = $NH_2$, n = 3, p = 3 |
| BA-TELO | R = $C_{12}H_{25}$, X = $NH_2$, n = 4, p = 3 |
| HE-TEDO | R = $C_{10}H_{21}$, X = OH, n = 2, p = 3 |
| PA-TEDO | R = $C_{10}H_{21}$, X = $NH_2$, n = 3, p = 3 |
| BA-TEDO | R = $C_{10}H_{21}$, X = $NH_2$, n = 4, p = 3 |
| HE-TECO | R = $C_8H_{17}$, X = OH, n = 2, p = 3 |
| PA-TECO | R = $C_8H_{17}$, X = $NH_2$, n = 3, p = 3 |
| BA-TECO | R = $C_8H_{17}$, X = $NH_2$, n = 4, p = 3 |

Nomenclature

The system of acronyms used to designate the compounds of Table I exemplifies the system of nomenclature used throughout. The acronyms HE, EA, BA, PA, FA, PMU, and DMA designate the $(CH2)_n$-X substituent of the above general structure. HE=hydroxyethyl, EA=ethylamine, BA=butylamine, PA=propylamine, FA=pentylamine, PMU=propylmethylurea, and DMA=dimethylamine.

Additionally, the first two letters of the acronyms MEMO, DEDO, DELO, DEMO, TELO, TEDO, and TECO define p, the number of (R—O—$(CH_2)_2$) ethers linked to the quaternary nitrogen, in the above general structure. Thus, in the compounds beginning with ME, p=1 (i.e. the compound is a monoether). In the compounds beginning with DE, p=2 (i.e. the compound is a diether). In the compounds beginning with TE, p=3 (i.e. the compound is a triether).

The second two letters of the acronyms MEMO, DEDO, DELO, DEMO, TELO, TEDO, and TECO identify the R group which is linked to the quaternary nitrogen through an ether in the general structure above. Thus, in the MO compounds, the ether linked R group is myristoyl, in the LO compounds R is lauryl, in the DO compounds R is decyl, and in the CO compounds R is capryl.

Cytofectins of the Invention: Structure

Some embodiments of the present invention are compounds having the formula

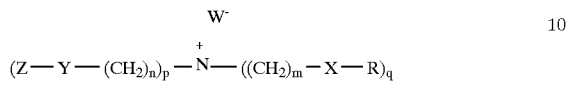

wherein
  R is H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups each of which may contain 0–5 heteroatoms;
  X is absent, O, N, NH, S, or Se;
  Y is absent, H, O, N, S, Se, NH or R as defined above;
  Z is H, O, N, S, NH, R as defined above, or an amino acid, peptide, polypeptide, protein, nucleic acid, nucleotide or nucleoside, polynucleotide, polynucleoside, mono-, di- or polysacchararide, or other bioactive or pharmaceutical agent or the following structure:

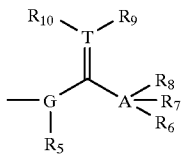

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;
  G is absent, O, N, NH, S, SH, Se, C, CH, or CR;
  T is O, N, S, Se, or C;
  A is O, N, S, Se, or C;
  W is a pharmaceutically acceptable anion.
  n is 0–10;
  m is 0–4;
  the sum of p and q is 4;
  wherein the compound is not a Rosenthal Inhibitor based cytofectin.

In a preferred embodiment of the structure above, X is O. In a further preferred embodiment, q is 1, 2, or 3. Advantageously, Z is H and Y is absent.

Another embodiment of the present invention is a compound of the formula

wherein
  $R_1$, $R_2$, and $R_3$ are independently H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups;
  $X_1$, $X_2$, and $X_3$ are independently absent or are H, O, N, NH, S or Se;
  R4 is H, OH, $NH_2$ or the following structure

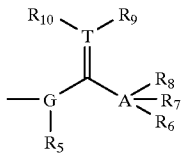

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;
  G is absent, O, N, NH, S, SH, Se, C, CH, or CR, where R is as defined for $R_1$, $R_2$, and $R_3$ above;
  T is O, N, S, Se, or C;
  A is O, N, S, Se, or C;
  m,p, and q are independently 0–4;
  n is 0–10;
  W is a pharmaceutically acceptable anion;
  wherein the compound is not a Rosenthal Inhibitor based cytofectin.

A further embodiment is a compound of the formula

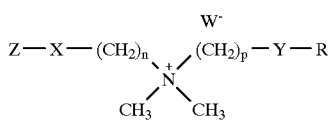

wherein
  X is absent, O, N, NH, S, or Se;
  Y is absent, O, N, NH, S, or Se;
  Z is H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups, or an amino acid, nucleotide, polynucleotide, mono-, di- or polysaccharide, or other bioactive or pharmaceutical agent or the following structure:

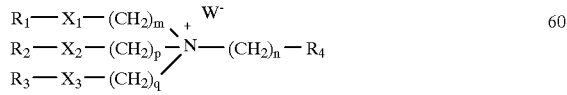

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR where R is as defined below;

T is O, N, S, Se, or C;

A is O, N, S, Se, or C;

R is H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups;

n is 0–10;

p is 0–4;

W is a pharmaceutically acceptable anion;

wherein the compound is not a Rosenthal Inhibitor based cytofectin.

In a preferred embodiment of the structure above, Y is O. In a further preferred embodiment of the structure above, p is 2.

In yet other preferred embodiments, the MEMO class of compounds, R is $C_{14}H_{29}$. Preferentially, in the structure above Z is H and X is selected from the group consisting of absent, O and NH. In further preferred compounds of the MEMO class n is 2–6.

Further embodiments of the invention are compounds of the DEXO series having the formula

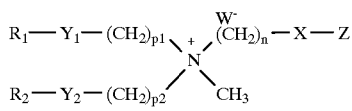

wherein

X is absent, O, N, NH S, or Se;

$Y_1$ and $Y_2$ are independently absent, O, N, NH, S, or Se;

Z is H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups, or an amino acid, nucleotide, polynucleotide, mono-, di- or polysaccharide, or other bioactive or pharmaceutical agent or the following structure:

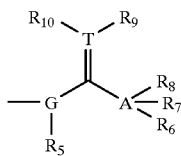

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR where R is as defined for $R_1$ and $R_2$ below;

T is O, N, S, Se, or C;

A is O, N, S, Se, or C;

$R_1$ and $R_2$ are independently H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups;

n is 0–10;

$p_1$ and $p_2$ are independently 0–4;

W is a pharmaceutically acceptable anion;

wherein the compound is not a Rosenthal Inhibitor based cytofectin.

In preferred embodiments of the above structure Y is O. In additional preferred DEXO compounds, $p_1$ and $p_2$ are 2.

Preferred compounds of the DEXO series are the DEDO class of compounds wherein R is $C_{10}H_{21}$. Preferred members of the DEDO class are those wherein Z is H and X is selected from the group consisting of absent, O and NH. In additional preferred DEDO compounds, n is 2–10. PA-DEDO, in which Z is H, X is NH, n is 3, $p_1$, and $p_2$ are 2, $Y_1$ and $Y_2$ are O, is the most active member of the DEDO class in the murine lung assay, although its activity in this assay is not as great as that of some members of the DELO class.

Further preferred embodiments of the DEXO series are the DELO class of compounds wherein R is $C_{12}H_{25}$. Advantageous members of the DELO class are those wherein Z is H and X is selected from the group consisting of absent, O and NH.

Additional advantageous DELO class compounds are those wherein n is 2–10. HA-DELO, in which Z is H, X is NH, n is 6, $p_1$ and $p_2$ are 2, and $Y_1$ and $Y_2$ are O, is particularly effective in the murine lung assay, exhibitting activity greater than numerous DEMO, DELO, DEDO, TELO, and TECO compounds against which it was compared. Gly-P-DELO, in which X is NH, Z is glycine amide, n is 3, and $Y_1$ and $Y_2$ are O, has also proven effective in the murine lung assay. PA-DELO, in which Z is H, X is NH, n is 3, $p_1$ and $p_2$ are 2, and $Y_1$ and $Y_2$ are O, has demonstrated efficacy in the porcine intraarterial assay.

Further preferred embodiments of the DEXO series are the members of the DEMO class in which R is $C_{14}H_{29}$. In preferred members of the DEMO class, Z is H and X is selected from the group consisting of absent, O and NH. In additional preferred members of the DEMO class n is 2–10. PA-DEMO, in which Z is H, X is NH, n is 3, $p_1$ and $p_2$ are 2, and $Y_1$ and $Y_2$ are O, has proven particularly effective in the murine intraperitoneal assay.

Additional embodiments of the present invention are the TEXO series of compounds having the formula

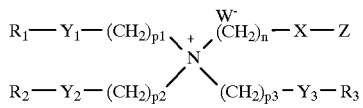

wherein

X is absent, O, N, NH, S, or Se;

$Y_1$, $Y_2$ and $Y_3$ are independently absent, O, N, NH, S, or Se;

Z is H, linear, branched, unsubstituted or substituted $C_1$–$C_{23}$alkyl, acyl, alkene, or heteroalkyl groups having from 0 to 6 sites of unsaturation and containing from 0 to 5 heteroatoms, or cyclic or aryl groups, or an amino acid, nucleotide, polynucleotide, mono-, di- or polysaccharide, or other bioactive or pharmaceutical agent or the following structure:

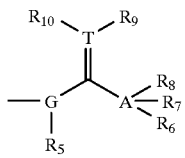

wherein $R_5$ through $R_{10}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or CR where R is as defined for $R_1$, $R_2$, and $R_3$ below;

T is O, N, S, Se, or C;

A is O, N, S, Se, or C;

$R_1$, $R_2$, and $R_3$ are independently H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups;

n is 0–10;

$p_1$, $p_2$ and $p_3$ are independently 0–4;

W is a pharmaceutically acceptable anion;

wherein the compound is not a Rosenthal Inhibitor based cytofectin.

Preferred members of the TEXO series are the TELO class of compounds wherein R is $C_{12}H_{25}$. Preferred TELO class compounds are those wherein Z is H and X is selected from the group consisting of absent, O and NH. In additional preferred TELO compounds, n is 2–10. PA-TELO, in which Z is H, X is NH, n is 3, $p_1$, $p_2$ and $p_3$ are 2, and $Y_1$, $Y_2$, and $Y_3$ are O has proven particularly effective in the Renca tumor assay.

Further preferred members of the TEXO series are the TEDO class of compounds wherein R is $C_{10}H_{21}$. In preferred TEDO compounds, Z is H and X is selected from the group consisting of absent, O and NH. Additional preferred TEDO compounds are those wherein n is 2–10.

Further preferred members of the TEXO series are the compounds of the TECO class wherein R is $C_8H_{17}$. In preferred TECO compounds, Z is H and X is selected from the group consisting of absent, O and NH. Additional preferred TECO compounds are those wherein n is 2–10.

The present invention also encompasses a method for delivering a molecule into a cell comprising the steps of (a) contacting the molecule with a formulation comprising an effective amount of the cationic lipid of Claim 1 to form a complex with the lipid; and (b) contacting a cell with the lipid complex formed in step (a);

whereby a biologically effective amount of the molecule is inserted into the cell.

In a preferred embodiment of the above method, the molecule delivered into the cell comprises an anionic molecule.

In some embodiments of the above method the formulation additionally includes one or more additional lipids. Preferentially, the additional lipids are selected from the group consisting of neutral lipids, phospholipids, and cholesterol.

In one embodiment of the above method the cells are in vitro. In another embodiment of the above method cells are in vivo.

In a preferred embodiment of the method wherein the cells are in vitro, the cells are used in an assay selected from the group consisting of murine lung transfection, murine intraperitoneal tumor, murine intramuscular, porcine or rabbit intraarterial, general subcutaneous tumor, or Renca tumor assays.

It is contemplated that any of the cytofectins described herein may be used in vitro, in vivo and in the various transfection assays described herein. All of these compounds may be made from known starting materials. Various compounds falling within the scope of the invention can be screened for activity by a person of ordinary skill in the art using the assays described in Examples 3, 6–10 or other standard transfection assays.

Bioactive HeadQroups on the Cytofectins (a) Targeting Species

A cytofectin according to the present invention can include a molecular species having a biological cell targeting activity as a terminal group. Within this class are cytofectins comprising cell receptor-specific molecules. Typically, the receptor-specific peptides or amino acids are linked as amides. Examples of preferred peptides which could be joined to the cytofectins of the present invention include the chemotactic peptides methionine-leucine-phenylalanine (Met-Leu-Phe), and pGlu-Pro-His. Other ligands for cell surface receptors that can be attached to cytofectins of the invention comprise peptidomimetic analogs; many viral attachment and internalization peptides, lactose and other di- and polysaccharides; acetylcholine analogs; and folic acid derivatives.

(b) Therapeutic Agents

A cytofectin according to the invention can include as a terminal group a bioactive molecular species. An example of a preferred bioactive species which could be linked to the compounds of the present invention is the thyrotropin-releasing hormone pGlutamate-histidine-proline.

(c) Cellular and Intracellular Targeting

A cytofectin according to the invention can comprise a terminal group bearing a ligand that can specifically bind to a cell membrane or intracellular target to effect a desired physiological response. Appropriate ligands may comprise peptides that are viral epitopes, hormones, enzyme substrates, monosaccharides, disaccharides, oligosaccharides, carbohydrates, cofactors, drugs, lectins, oligonucleotides, and nucleic acids. Preferred species among this group are cytofectins comprising chloroquine and other lysosomotropic agents, nuclear localization peptides, corticosteroids and viral peptides or proteins.

Groups Influencing Transfection Efficiency

The cytofectins of the present invention may be linked to groups which influence their transfection efficiencies. Such groups may be amino acids, peptides, polypeptides, proteins, nucleic acids, nucleotides, polynucleotides, mono, di- or polysaccharides. Both traditional and non-traditional linkages for appending these building blocks to the cytofectins are contemplated. Additionally, the amino acids, peptides, polypeptides, or proteins may include unusual or modified amino acids not generally found in living organisms. Such unusual or modified amino acids include but are not limited to the modified and unusual amino acids listed in 37 C.F.R. § 1.822. In addition, such amino acids may be synthetic amino acids not found in nature.

Reaction Schemes and Preparation Methods

B. Synthesis of Quaternary Cytofectins

A typical synthesis of a quaternary cytofectin, specifically [(3-aminopropyl)-(bis-(2-tetradecyloxyethyl)-methylammonium bromide] (PA-DEMO), is shown in Scheme I.

In accordance with Scheme I, an appropriate amine alcohol such as N-methyldiethanolamine is first reacted with a fatty acid sulfonate to form the corresponding fatty acid ether. Then, the resulting tertiary amine is alkylated using any appropriate reaction to add an additional alkyl chain or other derivatized moiety. This synthesis is disclosed in more detail in Example 1.

Note that the synthesis of quaternary cytofectins is not particularly involved. Conventional synthetic steps and readily-available reactants are utilized to form esters or ethers of the alcohol moieties of the tertiary amine starting material, and to add functional groups to what is ultimately a quaternary ammonium. Of course, conventional blocking or protecting steps can be used as appropriate during the synthesis, and thioethers, thioesters, and other analogues falling within the scope of the claim can be synthesized by conventional modifications of Scheme I.

The methods described above may be used to prepare a large number of cytofectins for screening in a reasonable period of time. Synthesis in conjunction with screening can be used to efficiently select the most effective cytofectin for a defined application.

Formulations

The compounds of the invention can be used in formulations to transfect mammalian cells both in vitro and in vivo. Formulations for transfection are known to those skilled in the art and are disclosed, together with methods for their preparation, for example, in U.S. Pat. No. 5,264,618 to Felgner, U.S. Pat. No. 5,334,761 to Gebeyehu et al, and Felgner et al. (*J. Biol. Chem.* 269:2550–2561, 1994), which are hereby incorporated by reference. The cationic lipids of the invention can be combined with amphipathic lipids such as phospholipids and with neutral lipids, such as cholesterol to form lipid vesicles, which can be liposomes, unilamellar vesicles, micelles, or simple films.

Cationic lipids of the invention are particularly useful in facilitating gene therapy. The use of cationic lipids for this purpose is reported by Nabel et al. (*Human Gene Therapy* 3:399–410, 1992).

The use of cationic liposomes is known to be useful for facilitating entry of polynucleotides, macromolecules, and small molecules into cells of the blood vessels, the systemic circulation, lung epithelial cells, brain tissue and frog embryos (Xenopus).

The present invention particularly contemplates the use of the disclosed cationic lipids to facilitate delivery of mRNA or DNA to living organisms, such as vertebrates, including birds, mammals, fish, and amphibians. Delivery to humans and domestic animals is specifically contemplated.

The polynucleotides preferably encode an immunogenic or therapeutic peptide or polypeptide. This method can thus be used for polynucleotide vaccinations as well as gene therapy. Where the cationic lipids of the present invention are used to introduce DNA into a host organism, the DNA may contain sequences in addition to the coding region such as suitable promoters such as the CMV, RSV or SV40 promoters, ribosome binding sites, and polyadenylation sites.

It is also noted that the cytofectins of the present invention are useful in transfecting cells in vitro. Although various compounds within the scope of the present invention are somewhat tissue specific in vivo, most or all are useful for transfection of cultured cells in vitro. For any particular candidate cytofectin of the present invention, its relative transfection efficacy in vitro and in various tissues in vivo can be readily ascertained using screening assays such as those disclosed in Examples 3, 6–10 or other standard transfection assays.

EXPERIMENTAL PROCEDURES

The chemical reactions described below are disclosed in terms of their general application to the preparation of the cationic lipids of the invention. Occasionally, the reaction may not be applicable as described to each molecular species within the disclosed scope. The compounds for which this occurs will be readily recognized by those skilled in the art. In all such cases, either the reactions can be successfully performed by conventional modifications known to those skilled in the art, that is, by changing to alternative conventional reagents, or by routine modification of reaction conditions. Alternatively, other reactions disclosed herein, in the references cited herein relating to the synthesis of other classes of cytofectins such as the DOTMA compounds of Felgner et al. *J. Biol. Chem.* 84:7413–7417, 1987, or in the conventional chemical literature will be applicable to the preparation of the compounds of the invention. In all preparative methods, all starting materials are known or readily preparable from known starting materials.

The present invention is described below in detail using the following examples, but the methods disclosed are applicable for the preparation of all cationic lipids covered by the scope of the invention and are not limited to the examples. All of the temperatures indicated in the Examples are in degrees Celsius and are uncorrected.

EXAMPLE 1

Synthesis of [(3-aminopropyl)-(bis-(2-tetradecyl oxyethyl))-methylammonium bromide] (PA-DEMO)

The synthesis of this quaternary cytofectin proceeds as shown in Scheme I, from N-methyldiethanolamine through DEMOA to γ-Phth-DEMO to PA-DEMO.

DEMOA

A dry vessel under an argon atmosphere was charged with 1.15 g (29 mmol, 2.2 eq) 60% sodium hydroxide in mineral oil. A positive argon pressure was maintained throughout the experiment. The mineral oil was removed by trituration with 3×12 mL dry hexane, then 80 mL anhydrous tetrahydrofuran were added and stirring was initiated. A solution of N-methyldiethanolamine (1.55 g, 13 mmol) in 15 mL anhydrous tetrahydrofuran was added dropwise to the magnetically stirred suspension at room temperature, followed by reflux overnight. A solution of tetradecyl methane sulfonate (9.37 g, 32 mmol, 2.5 eq) in 23 mL anhydrous tetrahydrofuran was added and the reaction was maintained at reflux for three days. The reaction mixture was then cooled, and the slurry vacuum filtered through a 0.75 cm pad of Celite. The reaction vessel and filtration apparatus were rinsed with 100 mL tetrahydrofuran. The combined filtrates were evaporated to yield the crude product which was purified using silica gel (4.5×35 cm bed) in conjunction with a step gradient of ethyl ether:hexane (10:90 to 100:0). Pure fractions were determined by aliquot thin layer chromatography (2:1 ether:hexane). These fractions were pooled, evaporated and resuspended in neat ether and dried with a small amount of magnesium sulfate. Filtration through a 0.2 μm PTFE filter, then rotary evaporation followed by high vacuum treatment yielded pure [bis-(2-tetradecyloxyethyl)-methyl amine] (DEMOA) (2.30 g, 35%).

γ-Phth-DEMO

A dry vessel under an argon atmosphere equipped with magnetic stirring was charged with 1.29 g (2.5 mmol) DEMOA, 1.36 g (5.1 mmol, 2.0 eq) N-(3-bromopropyl) phthalimide and 5 mL anhydrous dimethylformamide. The vessel was thoroughly flushed with argon, tightly stoppered and, after initiating magnetic stirring, heated to 110° C. for three days. The solution was cooled to ambient temperature, and the bulk of the solvent was removed from the crude product by vacuum distillation. The gummy residue was subjected to high vacuum overnight to remove minor entrained solvent, then purified using silica gel (3.5×33 cm bed) and isocratic elution with 90:10:0.25:0.25 chloroform:methanol:ammonium hydroxide:water. The pure fractions were pooled and evaporated. The residue was resuspended in neat chloroform, dried with a small amount of magnesium sulfate, filtered through 0.2 μm PTFE, then evaporated and treated with high vacuum, yielding 727 mg (37%) pure [(3-phthalylaminopropyl)-(bis-(2-tetradecyloxyethyl)-methylammonium bromide] (γ-Phth-DEMO).

PA-DEMO

A vessel equipped with magnetic stirring was charged with γ-Phth-DEMO (720 mg, 0.92 mmol), 13 mL anhydrous ethanol and stirring was initiated to dissolve the phthalate. The vessel was thoroughly flushed with argon, during which time 1 mL neat anhydrous hydrazine (32 mmol, 35 eq) was added. The vessel was tightly stoppered and allowed to stir overnight at ambient temperature. The thick slurry was filtered through a medium glass frit and 25 mL ethanol was used to rinse the vessel and filtration apparatus. The combined filtrates were evaporated and the residue partitioned between 100 mL chloroform and 50 mL 0.2 N sodium hydroxide. The phases were separated and the aqueous layer washed with an additional 25 mL chloroform. The combined organic phases were dried with sodium sulfate overnight. Gravity filtration through filter paper yielded a clear solution which was evaporated to afford a waxy solid which was resuspended in a minimal volume of neat chloroform, filtered through 0.2 μm PTFE, evaporated then treated with high vacuum, yielding the highly purified product [(3-aminopropyl)-(bis-(2-tetradecyl-oxyethyl))-methylammonium bromide] (PA-DEMO). Further purification can be accomplished by recrystallization from hexane.

It will be understood that quaternary cytofectins having different numbers of carbon atoms in their $R_1$ and $R_2$ chains may be prepared by substitution of the corresponding methane sulfonate in the preceding synthetic scheme. For example, to synthesize a cytofectin of the DEXO class in which $R_1=R_2=C_{12}H_{25}$, dodecylmethanesulfonate would be used in the reaction scheme in place of tetradecyl methanesulfonate.

It will also be understood that the reactions of synthesis of MEXO or TEXO compounds using the reactions in Scheme I merely requires the use of starting materials in which one or three alkoxy groups respectively are linked to the nitrogen.

EXAMPLE 2

Effect of Formulation on in vitro Transfection: Comparison of PA-DEMO with DMRIE Cytofectin: Solutions of a selected cytofectin in chloroform were prepared on a weight to volume (w/v) basis. Aliquots of cationic lipid and neutral lipid (when used) were transferred aseptically to sterile vials in amounts calculated to provide the relative and absolute lipid concentrations desired upon reconstitution with 1 ml of aqueous vehicle. Bulk chloroform was removed with a stream of dry nitrogen, and the vials were treated with high vacuum overnight to remove any residual solvent.

DNA-lipid complexes: Plasmid DNA at 5 mg/ml of phosphate buffered saline (PBS) as well as the dried, formulated cytofectin-neutral lipid mixture were suspended in OPTIMEM™ (Gibco BRL) and mixed together in 96 well plates at the desired mass/molar ratio as indicated in the Tables. The DNA-lipid complexes were added to the cells within 2 hours after mixing.

Transfection

Cell Lines: The cell lines used were obtained from the American Type Culture Collection (ATCC, Rockville, Md.) as follows: COS7 monkey kidney cells (ATCC CRL 1651); and $C2C_{12}$ mouse myoblast muscle cells (ATCC CRL 1772).

All cells were passaged 1:5 to 1:10 in 10% fetal bovine serum (FBS) and Dulbecco's Modified Eagles medium (DMEM). All cells were expanded through 10 doubling passages upon receipt and aliquots were stored frozen. Upon re-expansion, all cells were used for transfection studies before another 10 passages.

Transfection Assays: On day 0, 20,000 cells in 100 microliters 10% FEBS/90% DMEM were seeded into each well of 96-well culture plates (Nunc) and cultured overnight in a 5% $CO_2$ incubator at 37° C. On Day 1, the medium was aspirated carefully without dislodging cells, and 100 microliters of PA-DEMO/pRSV lacZ/DOPE in serum-free OPTI-MEM™ (A modification of MEM (Eagles) which contains HEPES buffer, 2,400 mg/L sodium bicarbonate, hypoxanthine, thymidine, sodium pyruvate, L-glutamine, trace elements, growth factors, and phenol red reduced to 1.6 mg/L, but no calcium chloride) (Gibco BRL) was added. DMRIE was used as a reference standard. The lacZ gene encodes the enzyme β-galactosidase which can be assayed colorimetricaly. The cationic lipid:DOPE ratios varied for each well. After 4 hours of culture, 50 microliters 30% FBS/70% OPTIMEM™ was added to each well. On Day 2, each well received 100 microliters 10% FEBS/90% OPTI-MEM™ (A modification of MEM (Eagles) which contains HEPES buffer, 2,400 mg/L sodium bicarbonate, hypoxanthine, thymidine, sodium pyruvate, L-glutamine, trace elements, growth factors, and phenol red reduced to 1.6 mg/L, but no calcium chloride). On Day 3, the medium was removed and 50 microliters lysis buffer (0.1% Triton-$X_1$00 in 250 mM Tris, pH 8.0) was added and the plates were stored at 70° C. for at least 20 hours. After thawing, the well media were assayed for their content of β-galactosidase enzyme activity according to Felgner et al. (*J. Biol. Chem.* 269:2550–2561, 1994).

The results (FIGS 1a–1d) show that total expression of β-gal in COS7 cells and $C2C_{12}$ cells was optimal at PA-DEMO:DOPE ratio of 75:25 and 50:50, respectively, while peak β-gal expression occurred in both cell lines when only PA-DEMO was used. Total β-gal expression in both cell lines was significantly decreased when the ratio of PA-DEMO:DOPE used was 25:75. PA-DEMO compared favorably with DMRIE in these in vitro assays. These experiments indicate that quaternary cytofectins promote efficient transfer of DNA across the cell membrane in vitro followed by functional expression of the gene within the cell. The screening assay used in these tests is useful for demonstrating transfection activity and for optimizing the cytofectin/colipid ratio.

EXAMPLE 3

Intralung Transfection Assay

Adult (4–16 weeks) female BALB/c mice were lightly anesthetized with metophane and 132 μg chloramphenicol acetyltransferase (CAT) DNA±cationic lipid in 100 μl USP saline or water was delivered intranasally using a disposable sterile, plastic insulin syringe fitted with a small plastic catheter. All fluids and syringes were equilibrated to room temperature and the delivery of the single 100 μl volume of DNA required less than one minute. Two or three days post-delivery, the mice were killed by sodium pentobarbital overdose, and the lungs extracted as follows.

Lungs were immediately frozen and stored at −78° C. Frozen lungs were individually pulverized into a fine powder by grinding over 0.4 ml frozen lysis buffer in a 1.5 ml tube using a reversible drill and a bit that just fits into the tube, and the powder is stored in the same tube at −78° C. until extraction. Frozen powders are thawed and 100 μl Reporter Lysis Buffer from Promega (Catalog #E397A) was added to each. The samples were vortexed for 15 minutes, frozen-thawed three times using alternating liquid nitrogen and room temperature water baths and centrifuged three minutes at 10,000×g. The supernatant was transferred to another 1.5 ml tube and the extraction process repeated (without freeze-thawing) after adding another 500 μl lysis buffer to the pellet. The second supernatant was combined with the first and stored at −78° C.

The cationic lipids used were as follows. From the DEMO class of compounds DMA-DEMO, HE-DEMO, and PA-DEMO having the structures defined above were tested. From the DELO class of compounds, DMA-DELO, EA-DELO, PA-DELO, BA-DELO, FA-DELO, and HA-DELO having the structures defined above were tested. From the DEDO class of compounds, HE-DEDO, EA-DEDO, PA-DEDO, BA-DEDO, and FA-DEDO having the structures defined above were tested. From the TELO class, HE-TELO, PA-TELO, and BA-TELO were analyzed. Finally, from the TECO class of compounds HE-TECO, PA-TECO, and BA-TECO were tested. GAP-DLRIE and DMRIE Br were tested for comparison.

CAT assays were performed by the radioactive partition method of Sankaran (Anal. Biochem., 200:180–186, 1992) or by using a CAT ELISA kit (Boehringer Mannheim, Indianapolis, Ind.). Briefly, CAT tissue homogenates were disrupted by freeze-thawing three times in an ethanol/dry ice bath. Cellular debris was removed by centrifugation and the protein extract was incubated with $^{14}$C-chloramphenicol and acetyl CoA. The chloramphenicol was extracted with ethyl acetate and thin layer chromatography was performed to determine the percent of $^{14}$C-chloramphenicol converted by the extracted cellular protein. Cell extracts were standardized to 2 μg protein incubated for 20 minutes. Tissue extracts were standardized to 200 μg protein incubated for four hours.

Standard curves were constructed using purified enzyme (Sigma, St. Louis, Mo.) spiked into lung extracts or enzyme provided in the ELISA kit. The two CAT assay methods yielded equivalent pg CAT per sample from the same set of extracts.

The results are summarized in FIG. 2. Of the DELO class of compounds, HA-DELO was the most effective, with FA-DELO, BA-DELO, and PA-DELO also exhibiting levels of activity at least 20% of that seen with GAP-DLRIE. Of the DEDO class of compounds, PA-DEDO was the most effective, exhibiting transfection efficiencies approximately 30% of that observed with GAP-DLRIE. EA-DEDO, BA-DEDO, and FA-DEDO also exhibited significant activity. The compounds of the TELO and TECO classes were inefficient in the murine lung assay system.

EXAMPLE 4

Effect of Distance Between Quaternary Nitrogen and Primary Amine

Figure 3:
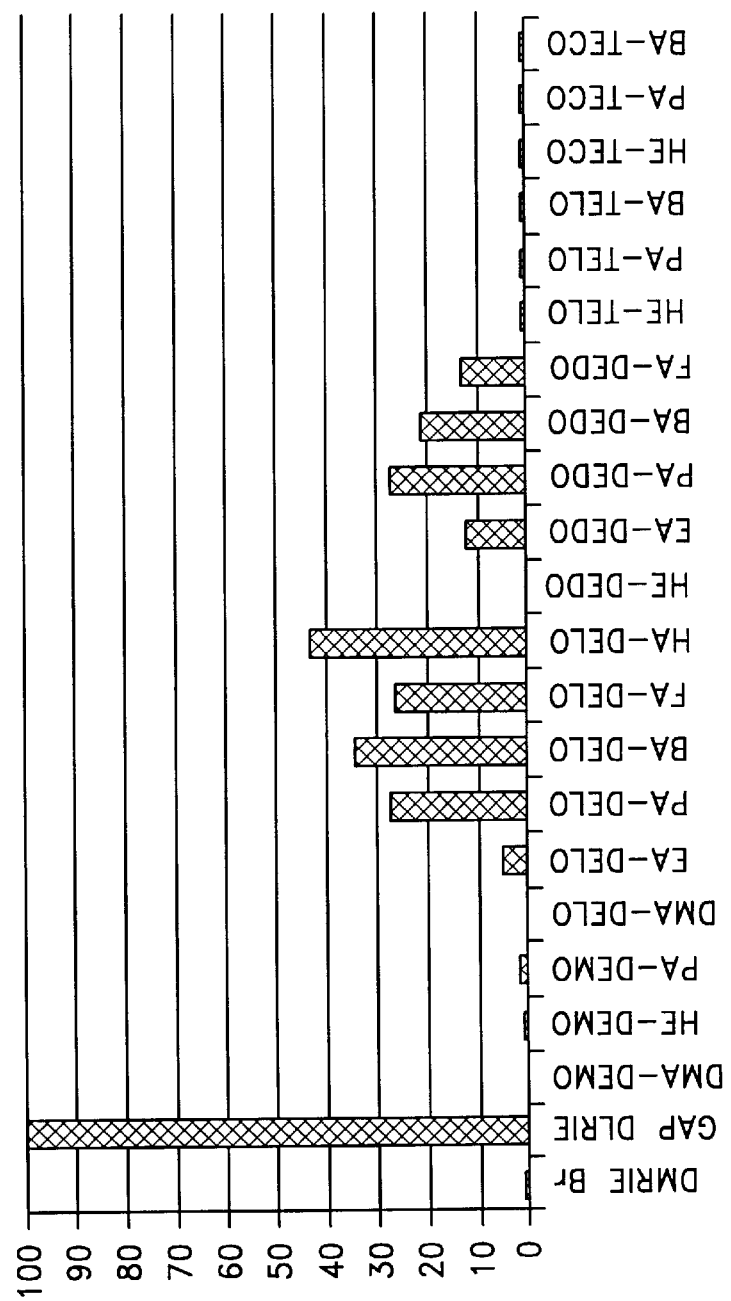
FIG. 3 compares the activities of numerous quaternary cytofectins of the DEMO, DELO, DEDO, TELO and TECO classes in vivo using the murine lung assay system.

As discussed above, the transfection efficiencies of cytofectins may be influenced by subtle changes in structure. In the experiments shown in FIG. 3, the spacing between a primary amine group and the quaternary nitrogen was varied in the members of the DELO class of compounds and the consequences on transfection efficiencies were determined in the intralung assay described in Example 3. FIG. 3 demonstrates the variability in transfection efficiencies resulting from such spacing differences. Of the spacings examined, a 6 carbon spacing provided the best transfection efficiency.

EXAMPLE 5

Effects of Alkyl Chain Length

Figure 4:
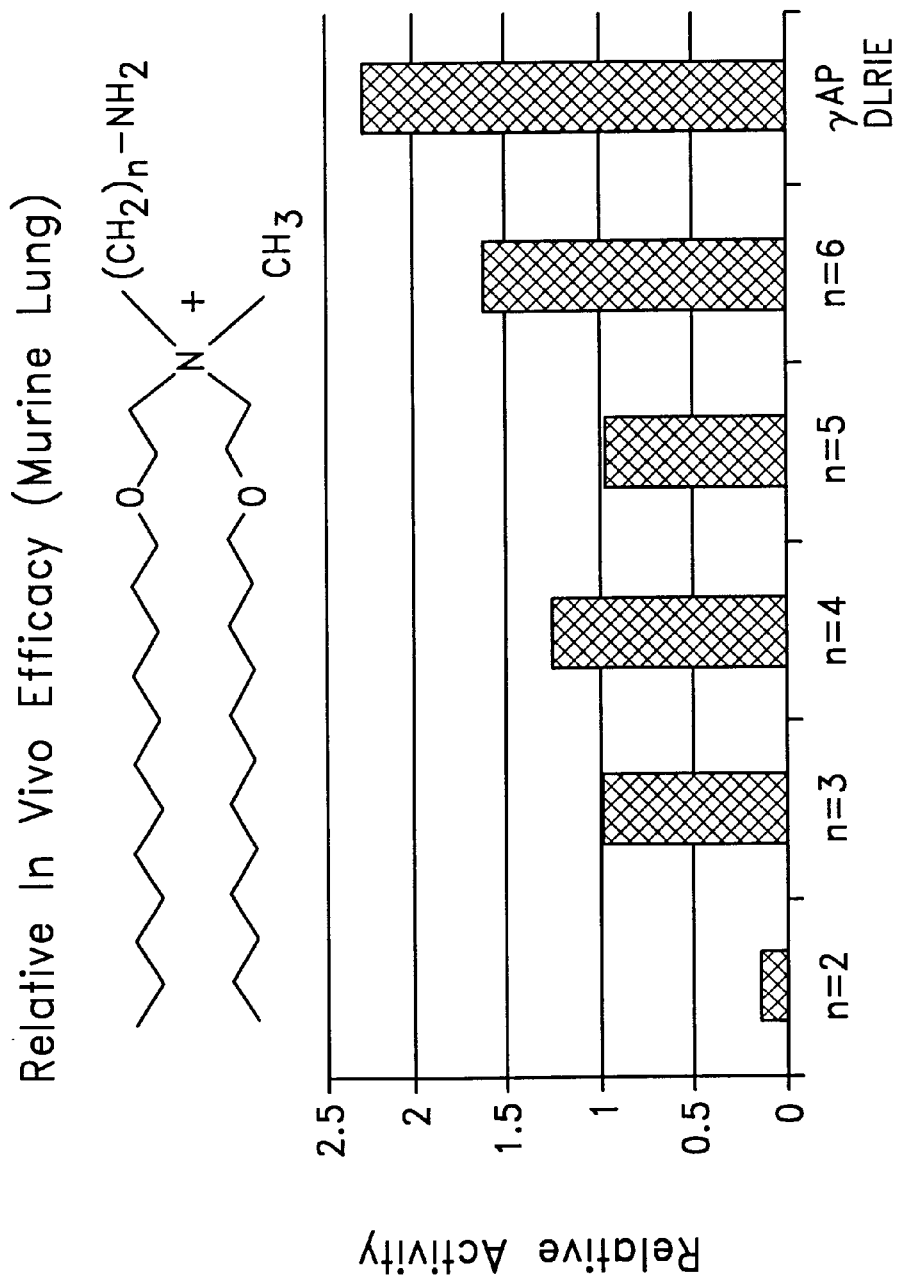
FIG. 4 compares the transfection efficiencies of members of the DELO class of compounds having a primary amine at varying distances from the quaternary nitrogen.

The effects of variation in chain length of the hydrophobic components of the quaternary cytofectins of the present invention were analyzed in the intralung assay described in Example 3. FIG. 4 shows that in the DEXO series of compounds, the DELO class of compounds (alkyl chain length $C_{12}$) exhibited significantly greater activity than the DEDO (alkyl chain length C10) or DEMO (alkyl chain length $C_{14}$) classes.

EXAMPLE 6

Analysis of Derivatized Cytofectins in the Intralung Assay

Figure 5:
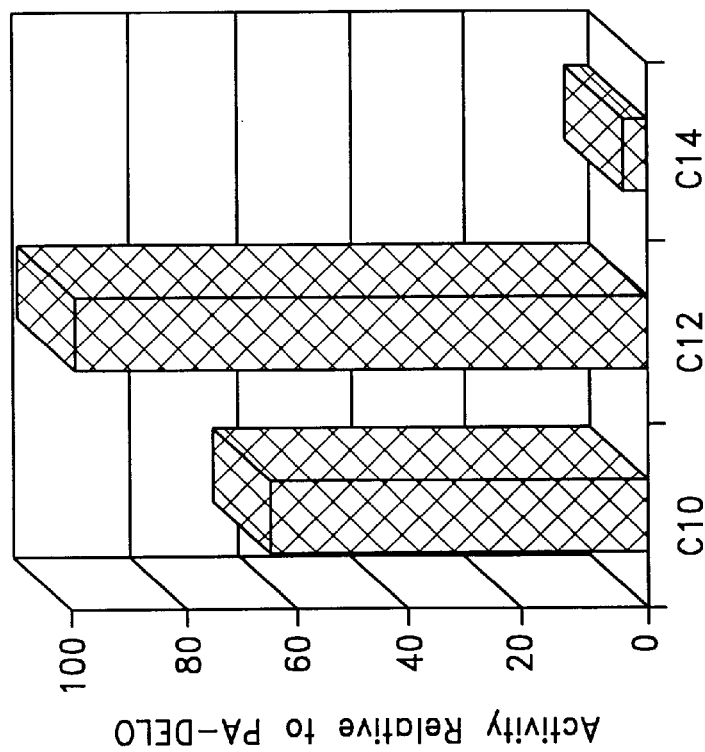
FIG. 5, shows the effects of variation in the chain length of the hydrophobic components of the quaternary cytofectins of the present invention for members of the DEXO series of compounds.
Figure 5:
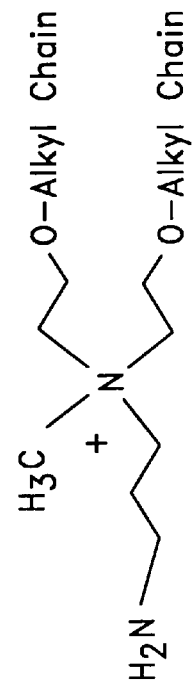

The activities of several derivatized cytofectins was assessed in the intralung assay described in Example 3. FIG. 5 shows that Gly-P-DELO exhibited the highest level of activity, approximately 70% of that obtained with GAP-DLRIE. PA-DELO and Orn-P-Delo provided approximately 30%. of the activity levels obtained with GAP-DLRIE. The remaining compounds provided between 5 and 15% the activity achieved with GAP-DLRIE. All derivatized cytofectins were significantly more active than DMRIE Br. Thus, FIG. 5 demonstrates that derivatized cytofectins provide a beneficial enhancement in transfection efficiency relative to DMRIE Br.

EXAMPLE 7

Intraperitoneal Tumor Assay Analysis of DELO, DEMO, and TELO Compounds

Figure 6:
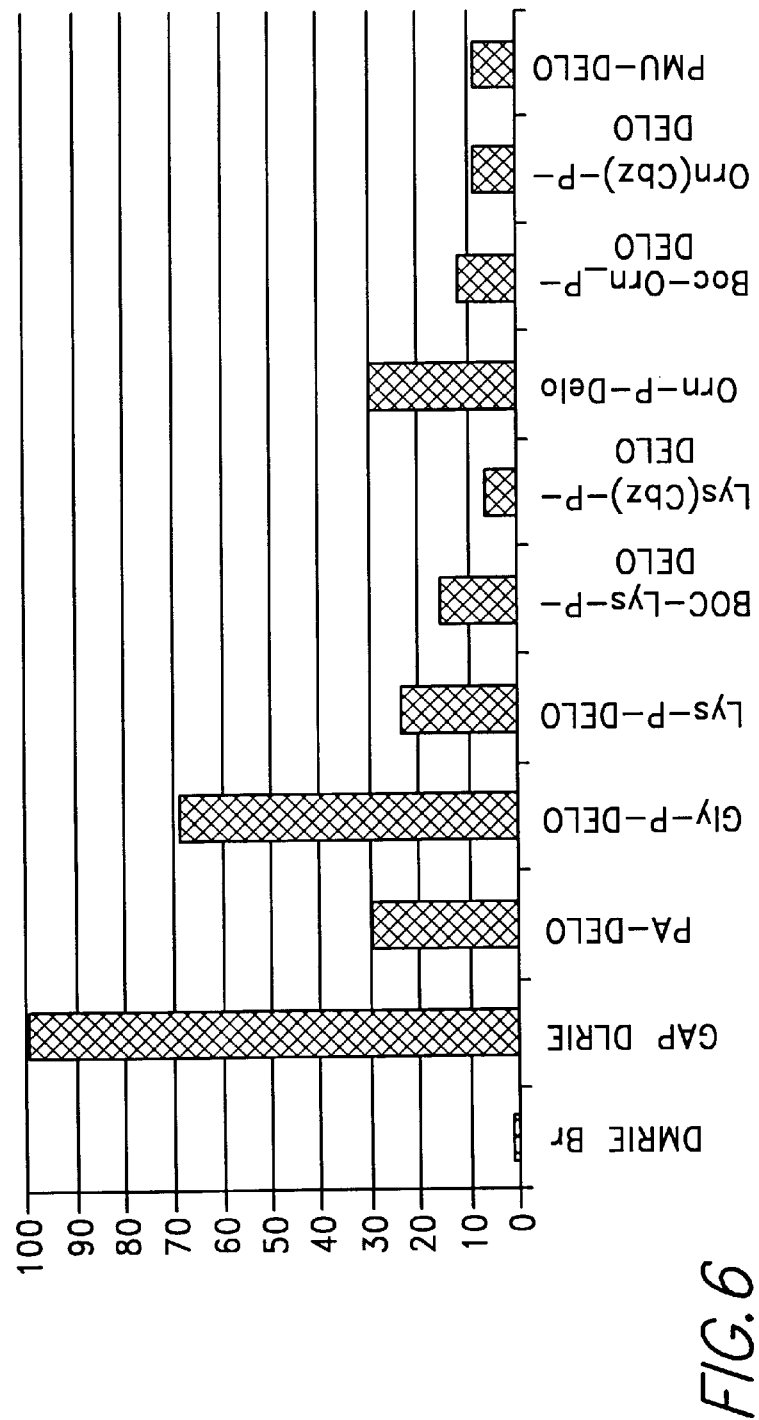
FIG. 6 compares the activities of numerous derivatized cytofectins in the intralung assay system.

The transfection efficiencies of several quaternary amine cytofectins were compared in the murine intraperitoneal model. Two hundred thousand murine B16 tumor cells in 500 μl RPMI were injected intraperitoneally into C57/B16 mice at day 0. At day 7–14 mice were injected intraperitoneally with a DNA/cytofectin/saline solution. In the experiment shown in FIG. 6, 0.5 mg of DNA was mixed with various cytofectins at a 10:1 molar ratio of DNA:cytofectin in 1.5 ml saline. Two days after injection of DNA, tumors were collected, extracted, and assayed for CAT activity as described above in EXAMPLE 3. FIG. 6 shows that compounds of the DELO, DEMO, and TELO classes were effective cytofectins, producing transfection efficiencies greater than that achieved by DNA alone. Of the compounds tested, PA-DEMO exhibited the highest transfection efficiency.

The tests reported here not only indicate that the claimed compounds are active in transfection, but also demonstrate how to select and optimize cytofectins for transfection of particular tissues. Although particular optimum structures are readily apparent for this assay, it will be appreciated that these results are tissue specific; in other words, even cytofectins that performed suboptimally in this assay have valuable activity in other assays, such as in vitro transfection, murine intraperitoneal tumor, murine intramuscular, porcine or rabbit intraarterial, general subcutaneous tumor, or Renca tumor assays.

EXAMPLE 8

Intramuscular Assay

The quadriceps of restrained, awake mice are injected with 50 µg luciferase or CAT DNA±cytofectin in 50 µl USP saline using a disposable sterile, plastic insulin syringe fitted with a 28G ½ needle (Becton-Dickinson) and a plastic collar cut from a yellow Eppendorf micropipette tip. The collar length is adjusted to limit the needle orifice penetration to a distance of about 2 mm into the central part of the 3 mm diameter rectus femoris muscle. Injection fluids and syringes are equilibrated to room temperature and injection of the single 50 µl volume of saline-DNA requires several seconds. The entire quadriceps muscle group (140–180 mg wet weight) is collected from each mouse leg at various times post-injection. Muscles are frozen and lysed as described in Example 3.

Luciferase activity is assayed using an automated microplate luminometer (Dynatech Model ML2250). One hundred µl of luciferase substrate is added by the luminometer's injection system to 20 µl extract and sample light units are recorded. The luciferse content of the samples is calculated from Relative light Units using a standard curve of purified firefly luciferase performed in the presence of uninjected muscle extract. The luciferase activity present in the injected muscle extract is much higher than in the uninjected muscle extract.

This assay illustrates another screening assay for optimizing the structure of a particular cytofectin for use in a particular tissue.

EXAMPLE 9

Intraarterial Assay

Arterial gene transfer was performed in Yorkshire pigs as follows. Arterial gene transfer was performed in the right and left iliofemoral arteries of each pig as described in Nabel, Science 249:1285–1288 (1990). Briefly, after anesthesia, the right and left iliofemoral arteries were exposed by surgical technique, and a double balloon catheter (USCI) was positioned in each artery. The artery was injured by inflating the proximal balloon to 500 mmHg for 1 minute. The catheter was then repositioned for performing gene transfer in the injured region of the artery. The arterial segment was flushed with vector solution consisting of the cytofectin being tested, the vector DNA, and OPTIMEM™ (A modification of MEM (Eagles) which contains HEPES buffer, 2,400 mg/L sodium bicarbonate, hypoxanthine, thymidine, sodium pyruvate, L-glutamine, trace elements, growth factors, and phenol red reduced to 1.6 mg/L, but no calcium chloride) (Gibco/BRL). For the experiment using DMRIE, a mixture of 100 µg DNA and 300 µg lipid was instilled. For the experiments using GAP-DLRIE and PA-DELO, a mixture of 100 µg DNA and 300 µg lipid was instilled. The vector solution was instilled into the site of injury for 20 minutes at 150 mmHg. Following instillation, the catheter was removed and the animal was allowed to recover. Forty eight hours after transfection the arteries were removed. Tissues were crushed using a glass pestle and subsequently freeze thawed three times. Samples were incubated 10 minutes at 65° C. to inactivate endogenous acetylase. Proteins were extracted and their concentration was determined using a calorimetric assay (Bio-Rad, Hercules, Calif.). In each assay 200 µg of total protein was assayed for CAT activity according to the procedure described above in Example 3 using a four hour incubation period.

Figure 7:
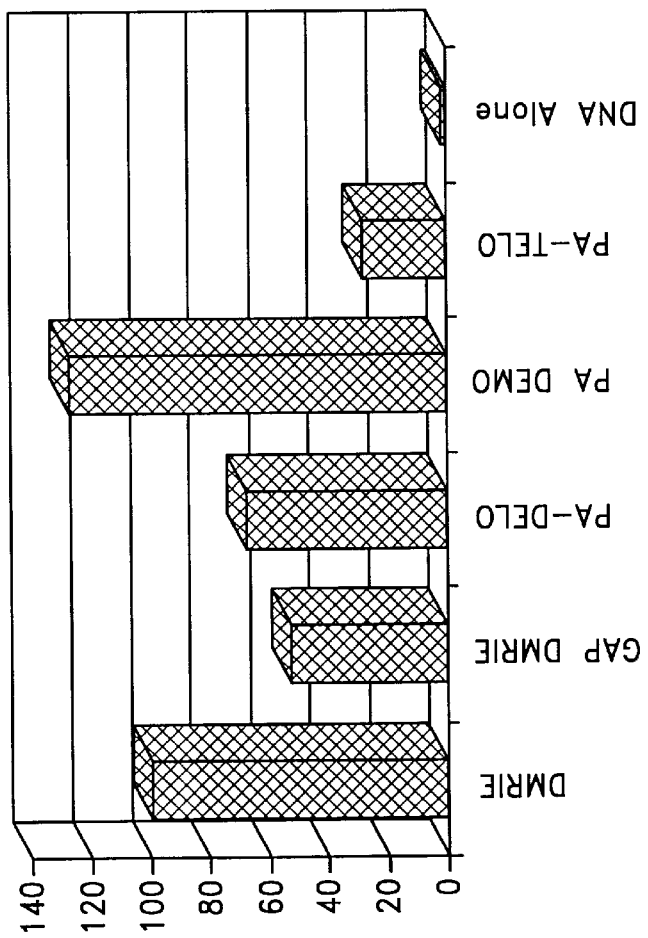
FIG. 7 compares the transfection efficiencies of cytofectins of the present invention in the intraperitoneal assay.
Figure 8:
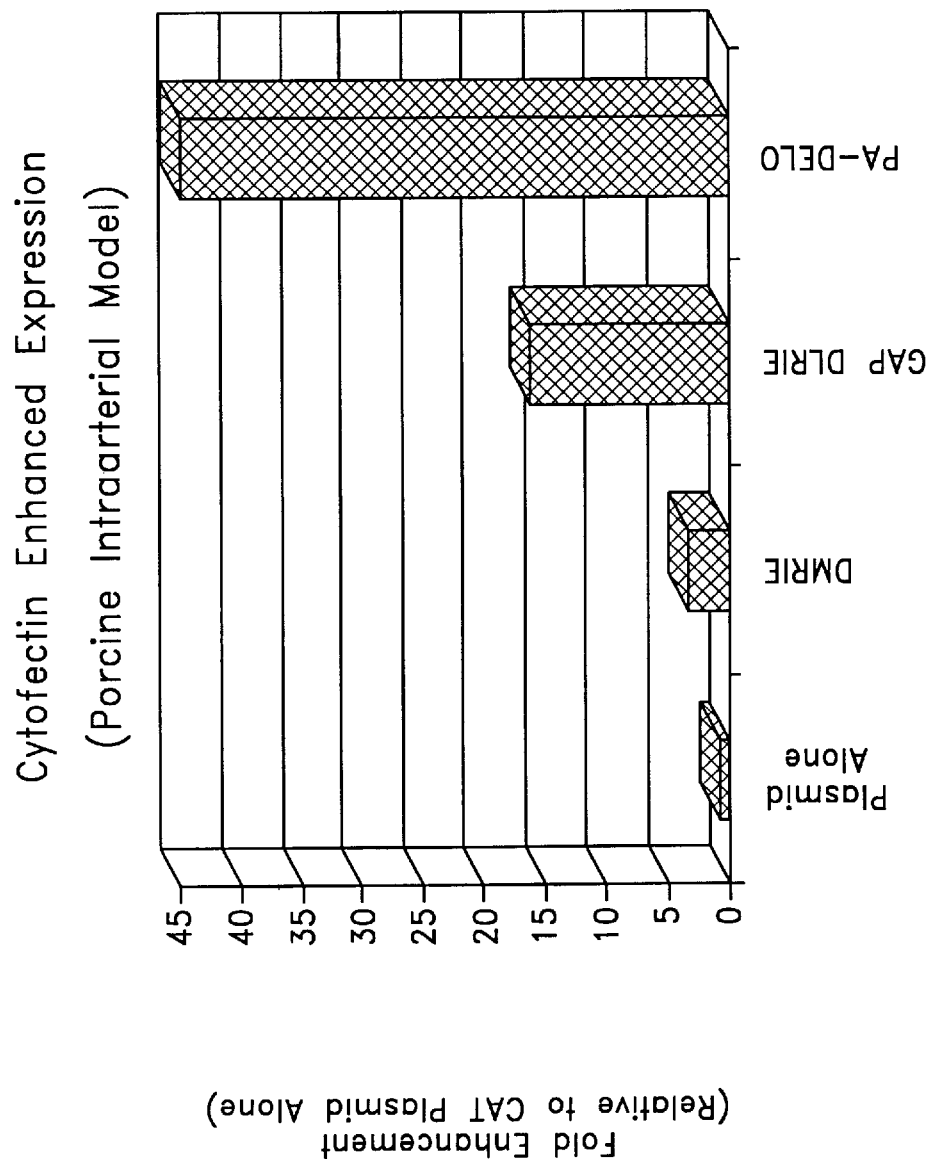
FIG. 8 compares the transfection efficiencies of several cytofectins in the porcine intraarterial assay.
Figure 9:
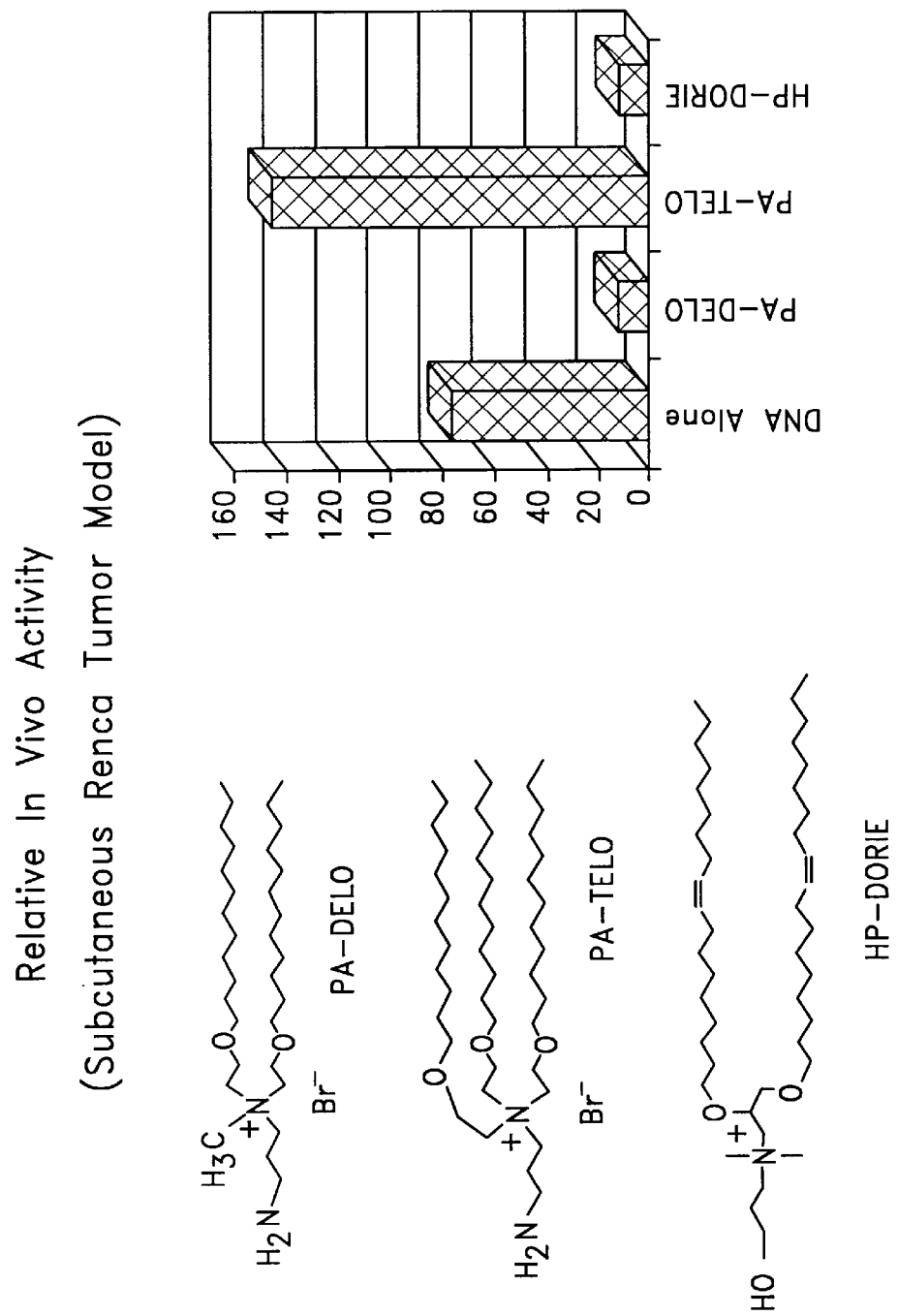
FIG. 9 compares the in vivo activities of PA-DELO, PA-TELO, and HP-DORIE relative to DNA alone in the subcutaneous Renca tumor model.

The results are shown in FIG. 7. PA-DELO exhibited significantly greater activity than DNA alone, DMRIE, or GAP DLRIE. The greater activity observed with PA-DELO relative to GAP-DLRIE in the intraarterial model contrasts with the results obtained in the murine lung model, where GAP-DLRIE was more active than PA-DELO (see FIG. 2). This result underscores the sensitivity cytofectins to the cell type to which they are applied.

Gene Transfer into Porcine Arteries and Atherosclerotic Rabbit Arteries

Liposome transfection of porcine arteries is performed by anesthesia, intubation and sterile exposure of the iliofemoral arteries as described. (Nabel et al., Science, 249:1285–1288, 1990). A double balloon catheter is inserted into the iliofemoral artery, and the proximal balloon is inflated to 500 mm Hg for 5 minutes. The balloon is deflated and the catheter is advanced so that the central space between the proximal and distal balloon is irrigated with heparinized saline. The CAT DNA solution (CAT DNA±cytofectin is instilled for 20 minutes in the central space of the catheter. The catheter is removed and antigrade blood flow is restored. Arteries are analyzed two days later for recombinant CAT expression. Arteries transfected with CAT DNA in the presence of cationic lipid exhibit a significant increase in CAT gene expression compared to arteries contacted with the DNA alone.

In vivo gene transfer of atherosclerotic rabbit iliac arteries is performed using a double injury model which is described by Faxon et al. (Arteriosclerosis, 4:189–195, 1984). After the second angioplasty injury is completed, the angioplasty balloon is withdrawn slightly so that the end hold infusion port of the catheter is at the proximal end of the injury. A ligature is placed at the distal end of the injury and the injured segment is flushed with heparinized saline and CAT DNA±cationic lipid liposome solution is instilled for 20 minutes into the isolated injured segment. The catheter is removed and antigrade blood flow is restored. Arteries are analyzed two days later for recombinant CAT expression. Arteries transfected with CAT DNA in the presence of cationic lipid exhibit a significant increase in CAT gene expression compared to arteries contacted with the DNA alone.

EXAMPLE 10

General Subcutaneous Tumor Transfection Assay

Tumors are prepared by injecting a suspension of tumor cells subcutaneously on the side of a mouse strain which is compatible with the specific tumor type. The tumors are periodically measured. Once they have reached a size suitable for injection, the tumor volume is approximated based on the measured diameter assuming a spherical tumor. A complex of the cytofectin to be evaluated with a plasmid encoding a reporter gene in a volume of saline equal to the volume of the tumor to be treated is then injected at a flow rate optimized for the particular tumor type. After an appropriate time, the tumors are collected, frozen, then ground up. The reporter gene product is subsequently extracted and the quantity which was expressed is determined using extraction and assay conditions appropriate for the particular gene product being used. A variety of tumor types may be evaluated using this general technique, and different reporter genes are more or less appropriate depending on the tumor type. A specific example of this assay involving Renca tumors is provided in Example 10 below.

EXAMPLE 12

Subcutaneous Renca Tumor Model

Renca tumors are propagated in 90% RPMI 1640/10% Fetal Bovine Serum. The tumors are injected subcutaneously into the side of BALB/C mice in 75 μL of a suspension containing approximately $10^6$ cells/mL tissue culture medium. When the tumors have reached 4.5 to 7 mm in diameter the volume of each individual tumor is calculated by measuring the diameter of the tumor and assuming a spherical tumor. For each individual tumor, a volume of the cytofectin/CAT plasmid complex in saline equivalent to the calculated volume of the tumor is injected into the tumor at a rate of 2 mL/min. After 48 hours, the tumors are collected, frozen, ground up, and extracted with 1.5 mL of extraction buffer as described in Example 3. CAT activity is quantitated as described in Example 3.

FIG. 7 shows the in vivo activities of PA-DELO, PA-TELO, and HP-DORIE relative to DNA alone in the Renca tumor model. In this assay system, PA-TELO provided significantly greater transfection efficiency than PA-DELO or HP-DORIE and over twice the activity of DNA alone.

Without further elaboration, it is believed that one skilled in the art can, using the preceding description, utilize the invention to its fullest extent. The invention may be embodied in other specific forms without departing from its spirit of essential characteristics. The described embodiments are to be considered in all respects only as illustrative and not restrictive, and the scope of the invention is therefore indicated by the appended claims rather than by the foregoing description. All modifications which come within the meaning and range of the lawful equivalency of the claims are to be embraced within their scope.

What is claimed is:

1. A quaternary nitrogen compound of the formula $$R_1-X_1-(CH_2)_m$$
$$R_2-X_2-(CH_2)_p-\overset{+}{N}-(CH_2)_n-R_4 \quad W^-$$
$$R_3-X_3-(CH_2)_q$$

wherein $R_1$ and $R_3$ are independently selected from the group consisting of linear $C_5-C_{23}$ groups or branched $C_5-C_{23}$ groups, said linear or branched $C_5-C_{23}$ groups being alkyl, acyl, alkene or heteroalkyl groups, said alkyl, acyl, alkene or heteroalkyl groups being unsubstituted or substituted, having from 0 to 6 sites of unsaturation, containing from 0 to 5 heteroatoms, or containing cyclic or aryl groups, said cyclic or aryl groups containing from 0 to 5 heteroatoms;

$R_2$ is independently selected from the group consisting of H, linear $C_5-C_{23}$ groups and branched $C_5-C_{23}$ groups, said linear or branched $C_5-C_{23}$ groups being alkyl, acyl, alkene or heteroalkyl groups, said alkyl, acyl, alkene or heteroalkyl groups being unsubstituted or substituted, having from 0 to 6 sites of unsaturation, containing from 0 to 5 heteroatoms, or containing cyclic or aryl groups, said cyclic or aryl groups containing from 0 to 5 heteroatoms;

$X_1$ and $X_3$ are independently selected from the group consisting of O, NH, S or Se;

$X_2$ is selected from the group consisting of absent O, NH, S, or Se;

$R_4$ is $NH_2$ m and q are independently 2–4;

p is 1–4;

n is 1–10;

W is a pharmaceutically acceptable anion;

wherein the compound is not a Rosenthal Inhibitor based cytofectin.

2. A quaternary nitrogen compound of the formula $$R_1-Y_1-(CH_2)_{p1}\underset{\underset{R_2-Y_2-(CH_2)_{p2}}{\diagup}}{\overset{+}{N}}\overset{(CH_2)_n-X-Z}{\diagdown}\quad W^-$$
$$\phantom{R_1-Y_1-(CH_2)_{p1}\overset{+}{N}}CH_3$$

wherein

X is NH;

$Y_1$ and $Y_2$ are independently O, NH, S, or Se;

Z is H;

$R_1$ and $R_2$ are independently selected from the group consisting of linear $C_5-C_{23}$ groups and branched $C_5-C_{23}$ groups, said linear or branched $C_5-C_{23}$ groups being alkyl, acyl, alkene or heteroalkyl groups, said alkyl, acyl, alkene or heteroalkyl groups being unsubstituted or substituted, having from 0 to 6 sites of unsaturation, containing from 0 to 5 heteroatoms, or containing cyclic or aryl groups, said cyclic or aryl groups containing from 0 to 5 heteroatoms;

n is 1–10;

$p_1$ is 2–4;

$p_2$ is 1–4;

W is a pharmaceutically acceptable anion;

wherein the compound is not a Rosenthal Inhibitor based cytofectin.

3. A compound according to claim 2 wherein $Y_1$ and $Y_2$ are O.

4. The compound of claim 3 wherein $p_1$ and $p_2$ are 2.

5. A compound according to claim 4 wherein $R_1$ and $R_2$ are $C_{10}H_{21}$.

6. A compound according to claim 5 wherein n is 2–10.

7. A compound according to claim 4 wherein $R_1$ and $R_2$ are $C_{12}H_{25}$.

8. A compound according to claim 7 wherein n is 2–10.

9. A compound according to claim 4 wherein $R_1$ and $R_2$ are $C_{14}H_{29}$.

10. A compound according to claim 9 wherein n is 2–10.

11. A method of delivering a molecule into a cell comprising the steps of (a) contacting the molecule with a formulation comprising an effective amount of any of the cationic lipids of claim 1 to form a complex with the lipid; and (b) contacting a cell with the lipid complex formed in step (a);

whereby a biologically effective amount of the molecule is inserted into the cell.

12. The method of claim 11 wherein the molecule is an anionic molecule.

13. The method of claim 11 wherein the formulation includes one or more additional lipids.

14. The method of claim 13 wherein the additional lipids are selected from the group consisting of neutral lipids, phospholipids, and cholesterol.

15. The method of claim 11, wherein the step of contacting said cell is performed under in vitro conditions.

16. The method of claim 11, wherein the step of contacting said cell is performned under in vivo conditions.

17. The method of claim 15, wherein said cells are in an assay selected from the group consisting of the murine lung transfection, murine intraperitoneal tumor, murine intramuscular, porcine intraarterial, rabbit intraarterial, Renca tumor, and subcutaneous tumor assays.

18. The method of claim 12 wherein the anionic molecule is mRNA.

19. The method of claim 12 wherein the anionic molecule is DNA.

20. A compound according to claim 9, wherein X is O, Z is H and n is 2.

21. A compound according to claim 1, wherein:

$R_1$ and $R_3$ are independently $C_8H_{17}$, $C_{10}H_{21}$, $C_{12}H_{25}$, or $C_{14}H_{29}$; and $R_2$ is H, $C_8H_{17}$, $C_{10}H_{21}$, $C_{12}H_{25}$, or $C_{14}H_{29}$.

22. The compound of claim 21, wherein $X_1$ and $X_3$ are O.

23. The compound of claim 22 wherein m and q are 2.

24. A compound according to claim 23 wherein $R_1$ and $R_3$ are $C_{10}H_{21}$.

25. A compound according to claim 24 wherein n is 2–10.

26. A compound according to claim 23 wherein $R_1$ and $R_2$ are $C_{12}H_{25}$.

27. A compound according to claim 23 wherein n is 2–10.

28. A compound according to claim 23 wherein $R_1$ and $R_2$ are $C_{14}H_{29}$.

29. A compound according to claim 28 wherein n is 2–10.

30. A compound according to claim 1 wherein $R_1$, $R_2$ and $R_3$ are independently $C_8H_{17}$, $C_{10}H_{21}$, $C_{12}H_{25}$, or $C_{14}H_{29}$.

31. The compound of claim 30, wherein $X_1$, $X_2$ and $X_3$ are O.

32. A compound according to claim 31 wherein m, p and q are 2.

33. A compound according to claim 32 wherein $R_1$, $R_2$, and $R_3$ are $C_{12}H_{25}$.

34. A compound according to claim 33 wherein n is 2–10.

35. A compound according to claim 32 wherein $R_1$, $R_2$, and $R_3$ are $C_{10}H_{21}$.

36. A compound according to claim 35 wherein n is 2–10.

37. A compound according to claim 32 wherein $R_1$, $R_2$, and $R_3$ are $C_8H_{17}$.

38. A compound according to claim 37 wherein n is 2–10.

* * * * *